(12) United States Patent
Casellas et al.

(10) Patent No.: US 7,825,112 B2
(45) Date of Patent: Nov. 2, 2010

(54) 2-CARBAMIDE-4-PHENYLTHIAZOLE DERIVATIVES, PREPARATION THEREOF AND THERAPEUTIC USE THEREOF

(75) Inventors: Pierre Casellas, Montpellier (FR); Daniel Floutard, Combaillaux (FR); Pierre Fraisse, Juvignac (FR); Stephane Hourcade, Montpellier (FR); Samir Jegham, Montferrier-sur-Lez (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/146,898

(22) Filed: Jun. 26, 2008

(65) Prior Publication Data
US 2009/0018117 A1 Jan. 15, 2009

Related U.S. Application Data

(63) Continuation of application No. PCT/FR2007/000007, filed on Jan. 4, 2007.

(30) Foreign Application Priority Data
Jan. 6, 2006 (FR) .................................. 06 00117

(51) Int. Cl.
*A61K 31/551* (2006.01)
*A61K 31/496* (2006.01)
*A61K 31/427* (2006.01)
*C07D 277/44* (2006.01)
*C07D 417/12* (2006.01)
*C07D 417/14* (2006.01)

(52) U.S. Cl. ............... 514/218; 514/253.1; 514/254.02; 540/575; 544/364; 544/369

(58) Field of Classification Search ........................ None
See application file for complete search history.

(56) References Cited

U.S. PATENT DOCUMENTS

| 4,225,610 | A | 9/1980 | Tarayre et al. |
| 5,314,889 | A | 5/1994 | Boigegrain et al. |
| 6,506,751 | B1 | 1/2003 | Justus et al. |
| 2002/0115863 | A1 | 8/2002 | Patel et al. |
| 2002/0119962 | A1 | 8/2002 | Jacobs et al. |
| 2004/0048891 | A1 | 3/2004 | Kato et al. |
| 2006/0135575 | A1 | 6/2006 | Carayon et al. |
| 2007/0179126 | A1 | 8/2007 | Casellas et al. |
| 2007/0259847 | A1 | 11/2007 | Casellas et al. |

FOREIGN PATENT DOCUMENTS

| EP | 0 001 727 A2 | 5/1979 |
| EP | 0 518 731 | 12/1992 |
| EP | 0 519 449 | 12/1992 |
| EP | 1 344 525 A1 | 9/2003 |
| WO | WO 87/01706 | 3/1987 |
| WO | WO 93/00342 | 1/1993 |
| WO | WO 02/051397 | 7/2002 |
| WO | WO 03/015778 | 2/2003 |
| WO | WO 03/057145 A2 | 7/2003 |
| WO | WO 03/088908 A2 | 10/2003 |
| WO | WO 03/104230 A1 | 12/2003 |
| WO | WO 2004/096798 | 11/2004 |
| WO | WO 2006/016039 A1 | 2/2006 |
| WO | WO 2006/042954 A1 | 4/2006 |
| WO | WO 2006/067401 A1 | 6/2006 |
| WO | 2008/064054 | * 5/2008 |

OTHER PUBLICATIONS

Vippagunta et al. Advanced Drug Delivery Reviews, vol. 48, pp. 3-26 (2001).*
Abdel-Magid et al, Reductive Amination of Aldehydes and Ketones by Using Sodium Triacetoxyborohydride, Tetrahedron Letters, 1990 (31) 39 pp. 5595-5598.
Abdel-Magid et al, Reductive Amination of Aldehydes and Ketones with Sodium Triacetoxyborohydride. Studies on Direct and Indirect Reductive Amination Procedures, J. Org. Chem., 1996 (61) pp. 3849-3862.
Amato et al, Acrylate as an Efficient Dimethylamine Trap for the Practical Synthesis of 1-tert-Butyl-4-piperidone via Transamination, Org. Process R&D, 2004 (8) pp. 939-941.
Casy et al, Preparation of 3-Substituted 4-Thianones and Their 1,1-Dioxides via Palladium Mediated Deallyloxycarbonylation, Synthesis, 1989 pp. 767-769.
Paavola et al, Monomeric Monocyte Chemoattractant Protein-1 (MCP-1) Binds and Activates the MCP-1 Receptor CCR2B, J. Bio. Chem., 1998 (273) 50 pp. 33157-33165.
Taylor et al, Novel 5-Desmethylene Analogues of 5,10-Dideaza-5,6,7,8-tetrahydrofolic Acid as Potential Anticancer Agents, J. Org. Chem., 1992 (57) pp. 3218-3225.
Watson, Novel Methodology for the Preparation of 5-Substituted Tetrahydro[2,3-D]Pyrimidines, Synthetic Communications, 1998 (28) 10 pp. 1897-1905.

(Continued)

*Primary Examiner*—Emily Bernhardt
(74) *Attorney, Agent, or Firm*—Kelly L. Bender; R. Brian McCaslin

(57) ABSTRACT

The disclosure relates to 2-carbamide-4-phenylthiazole derivatives having the following general formula (I):

wherein $R_1$, $R_2$, $R_3$, Y and p are as defined in the disclosure. The disclosure also relates to pharmaceutical compositions containing a compound of formula (I), to processes for preparing the compounds of formula (I), and to methods of using the compounds of formula (I).

17 Claims, No Drawings

OTHER PUBLICATIONS

Zaragoza et al, 1-Alkyl-4-acylpiperazines as a New Class of Imidazole-Free Histamine H3 Receptor Antagonists, J. Med. Chem., 2004 (47) pp. 2833-2838.

Allen et al, Discovery And SAR Of Trisubstituted Thiazolidinones As CCR4 Antagonists, Bioorganic & Medicinal Chemistry Letters, Apr. 2004, 14:1619-1624.

Byrn et al, Hydrates and Solvates, Solid-State Chemistry of Drugs, Second Edition, 1999, pp. 233-247.

Lombardino et al, Potent Antiinflammatory N-Heterocyclic 3-Carboxamides of 4-Hydroxy-2-methyl-2H-1,2-benzothiazine 1,1-Dioxide, J. Med. Chem., 16 (5) pp. 493-496 (1973).

* cited by examiner

2-CARBAMIDE-4-PHENYLTHIAZOLE DERIVATIVES, PREPARATION THEREOF AND THERAPEUTIC USE THEREOF

The invention relates to 2-carbamide-4-phenylthiazole derivatives, to the preparation thereof and to the therapeutic application thereof.

The invention concerns compounds corresponding to formula (I) below:

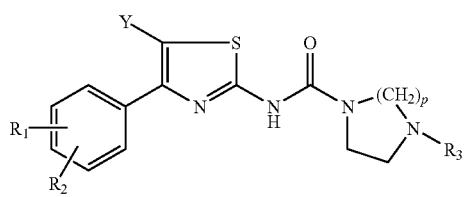

wherein:
- $R_1$ represents a hydrogen atom, a halogen atom, a $(C_1\text{-}C_8)$ alkyl, trifluoro$(C_1\text{-}C_4)$alkyl, —OH, —O—$(C_1\text{-}C_8)$ alkyl, —O-trifluoro$(C_1\text{-}C_8)$alkyl, —O—$(C_1\text{-}C_8)$alkyl-$(C_3\text{-}C_{10})$cycloalkyl, —O—$(C_3\text{-}C_{10})$cycloalkyl, —O—CH$_2$—CH=CH$_2$ or —S—$(C_1\text{-}C_4)$alkyl group;
- $R_2$ represents a hydrogen atom, a halogen atom, an —OH, $(C_1\text{-}C_8)$alkyl, trifluoro$(C_1\text{-}C_4)$alkyl, perfluoro$(C_1\text{-}C_4)$ alkyl, $(C_3\text{-}C_{10})$cycloalkyl, —O—$(C_1\text{-}C_8)$alkyl, —O—$(C_1\text{-}C_8)$alkyl$(C_3\text{-}C_{10})$cycloalkyl, —O—$(C_3\text{-}C_{10})$cycloalkyl, —O—CH$_2$—CH=CH$_2$ or —$(C_1\text{-}C_8)$alkyl $(C_3\text{-}C_8)$cycloalkyl group;
- Y represents a hydrogen atom or a halogen atom;
- p represents 2 or 3;
- $R_3$ represents:

a1) a group of formula —(CH$_2$)$_a$-A in which a represents 1, 2, 3 or 4, and A is selected from the group constituted by:

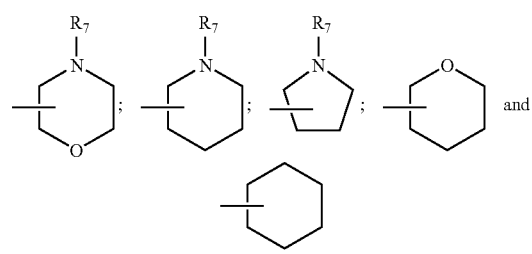

in which $R_7$ is selected from the group constituted by —$(C_1\text{-}C_8)$alkyl-COO—$(C_1\text{-}C_8)$alkyl, —CO—$(C_1\text{-}C_8)$alkyl in which the alkyl is substituted with at least one halogen atom, —$(C_3\text{-}C_{10})$cycloalkyl, phenyl, —COO—$(C_3\text{-}C_{10})$cycloalkyl, —SO$_2$—$(C_1\text{-}C_8)$alkyl in which the alkyl group is substituted with at least one halogen atom, —SO$_2$-phenyl in which the phenyl is substituted with at least one —O—$(C_1\text{-}C_8)$alkyl group, —SO$_2$-heteroaryl in which the heteroaryl is a pyrazole, an isoxazole or an imidazole and in which it is independently substituted with at least one group selected from halogen or —$(C_1\text{-}C_8)$alkyl, —SO$_2$—N(($C_1\text{-}C_8$)alkyl)$_2$, —SO$_2$—OH, —SO$_2$—($C_3\text{-}C_{10}$)cycloalkyl, —CO—NH(($C_1\text{-}C_8$)alkyl), —$(C_1\text{-}C_8)$alkyl-CN, —$(C_1\text{-}C_8)$alkylimidazole, —$(C_1\text{-}C_8)$alkyl-COOH, —$(C_1\text{-}C_8)$alkyl-COO$^-$M$^+$, —$(C_1\text{-}C_8)$alkyl-OH, —$(C_1\text{-}C_8)$alkyltetrazole, —$(C_1\text{-}C_8)$alkyl-CO—NH$_2$, —$(C_1\text{-}C_8)$alkyl-CO—NH(($C_1\text{-}C_8$)alkyl), —$(C_1\text{-}C_8)$alkyl-CO—NH(($C_3\text{-}C_{10}$)cycloalkyl), —$(C_1\text{-}C_8)$ alkyl-CO—N(($C_1\text{-}C_8$)alkyl)(($C_3\text{-}C_{10}$)cycloalkyl), —$(C_1\text{-}C_8)$ alkyl-CO—N(($C_1\text{-}C_8$)alkyl)$_2$, —$(C_1\text{-}C_8)$alkyl-CO—N(($C_3\text{-}C_{10}$)cycloalkyl)$_2$, in which M$^+$ is an alkali metal cation selected from Li$^+$, Na$^+$ and K$^+$, and when two alkyl or cycloalkyl substituents are bonded to the nitrogen atom, they may be independently identical or different;

a2) a group of formula —CO(CH$_2$)$_b$-A in which b represents 0, 1, 2, 3 or 4, and A is selected from the group constituted by:

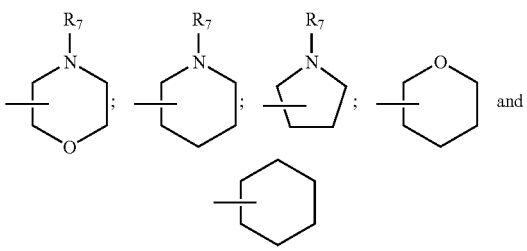

in which $R_7$ is as defined above;

a3) a group —B in which B is selected from the group constituted by:

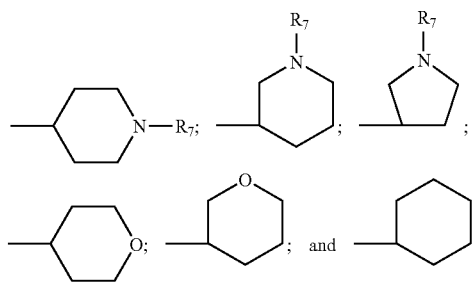

in which $R_7$ is as defined above;

a4) a group of formula —(CH$_2$)$_a$—C in which a represents 1, 2, 3 or 4, and C is selected from the group constituted by:

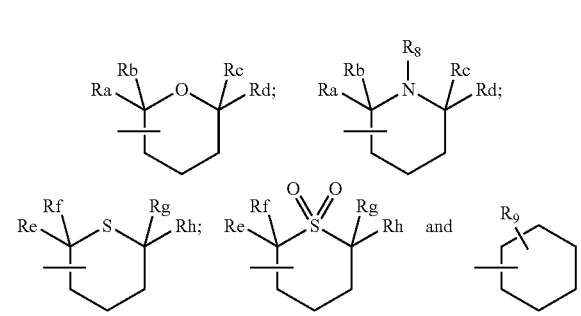

in which:
- $R_8$ is selected from the group constituted by a hydrogen atom, a $(C_1\text{-}C_8)$alkyl, —$(C_1\text{-}C_8)$alkyl-COO—$(C_1\text{-}C_8)$ alkyl, —CO—$(C_1\text{-}C_8)$alkyl group in which the alkyl is optionally substituted with at least one halogen atom, —(C$_3$-C$_{10}$)cycloalkyl, phenyl, —COO—(C$_3$-C$_{10}$)cycloalkyl, —SO$_2$—(C$_1$-C$_8$)alkyl in which the alkyl is optionally substituted with at least one halogen atom, —SO$_2$-phenyl in which the phenyl is optionally substituted with at least one —O—(C$_1$-C$_8$)alkyl group, —SO$_2$-heteroaryl in which the heteroaryl is a pyrazole, an isoxazole or an imidazole and in which it is optionally independently substituted with at least one group selected from halogen or —(C$_1$-C$_8$)alkyl, —SO$_2$—N((C$_1$-C$_8$)alkyl)$_2$, —SO$_2$—OH, —SO$_2$—(C$_3$-C$_{10}$)cycloalkyl, —CO—NH((C$_1$-C$_8$)alkyl), —(C$_1$-C$_8$)alkyl-CN, —(C$_1$-C$_8$)alkylimidazole, —(C$_1$-C$_8$)alkyl-COOH, —(C$_1$-C$_8$)alkyl-COO$^-$M$^+$, —(C$_1$-C$_8$)alkyl-OH, —(C$_1$-C$_8$)alkyltetrazole, —(C$_1$-C$_8$)alkyl-CO—NH$_2$, —(C$_1$-C$_8$)alkyl-CO—NH((C$_1$-C$_8$)alkyl), —(C$_1$-C$_8$)alkyl-CO—NH((C$_3$-C$_{10}$)cycloalkyl), —(C$_1$-C$_8$)alkyl-CO—N((C$_1$-C$_8$)alkyl)((C$_3$-C$_{10}$)cycloalkyl), —(C$_1$-C$_8$)alkyl-CO—N((C$_1$-C$_8$)alkyl)$_2$, —(C$_1$-C$_8$)alkyl-CO—N((C$_3$-C$_{10}$)cycloalkyl)$_2$, in which M$^+$ is an alkali metal cation selected from Li$^+$, Na$^+$ and K$^+$, and when two alkyl or cycloalkyl substituents are bonded to a nitrogen atom, they may be independently identical or different;

R$_9$ is selected from the group constituted by: hydroxyl, O—(C$_1$-C$_8$)alkyl, —O-trifluoro(C$_1$-C$_8$)alkyl, —O—(C$_1$-C$_8$)alkyl(C$_3$-C$_{10}$)cycloalkyl, —O—(C$_3$-C$_{10}$)cycloalkyl;

Ra, Rb, Rc and Rd are independently a hydrogen atom or a methyl group, given that at least one of Ra, Rb, Rc and Rd is a methyl group;

Re, Rf, Rg and Rh are independently a hydrogen atom or a methyl group;

a5) a group of formula —CO(CH$_2$)$_b$—C in which b represents 0, 1, 2, 3 or 4, and C is selected from the group constituted by:

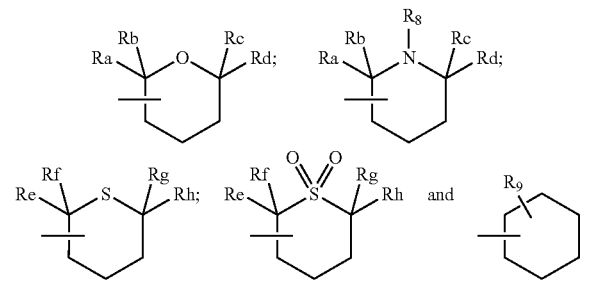

in which:
R$_8$, R$_9$, Ra, Rb, Rc, Rd, Re, Rf, Rg and Rh are as defined above;

a6) a group -D wherein D is selected from the group constituted by:

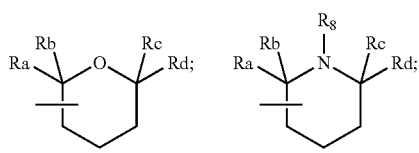

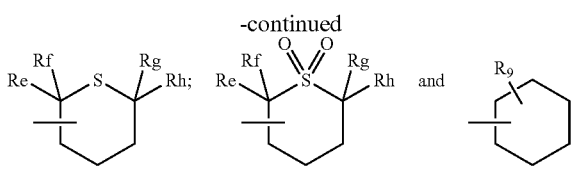

in which:
R$_8$, R$_9$, Ra, Rb, Rc, Rd, Re, Rf, Rg and Rh are as defined above; constituted as a base or an addition salt with an acid, as well as constituted as hydrates or solvates.

A preferred halogen is a fluorine.

The compounds of formula (I) may contain one or more asymmetrical carbon atoms. They may thus exist in the form of enantiomers or diastereoisomers. Said enantiomers, diastereoisomers and mixtures thereof, including racemic mixtures, are encompassed by the invention.

The compounds of formula (I) may exist as bases or addition salts with the acids. Said addition salts are encompassed by the invention.

Said salts are advantageously prepared with pharmaceutically acceptable acids, but the invention also encompasses salts of other acids used, for example, in purifying or isolating compounds of formula (I).

The compounds of formula (I) may also exist in the form of hydrates or solvates, namely in the form of associations or combinations with one or more molecules of water or with a solvent. The invention also encompasses such hydrates and solvates.

The following definitions are used in the present invention:
C$_{t-z}$, in which t and z may take values of 1 to 10, means a carbonaceous chain which may contain t to z carbon atoms, for example C$_{1-3}$ means a carbonaceous chain which may contain 1 to 3 carbon atoms;

a halogen atom means, for example, a fluorine, a chlorine, a bromine or an iodine;

an alkyl group: a linear or branched, saturated aliphatic group optionally substituted with a halogen atom. Examples which may be cited are methyl, ethyl, propyl, isopropyl, butyl, isobutyl, tertbutyl, pentyl, 2-fluoroethyl groups, etc;

a cycloalkyl group: a cyclic alkyl group. Examples which may be cited are cyclopropyl, cyclobutyl, cyclopentyl, cyclohexyl groups, etc;

a perfluoroalkyl group: an alkyl radical, as defined above, wherein all of the carbon atoms have been substituted with fluorine atoms.

The compounds encompassed by the subject-matter of the invention which may be cited include those of formula (I.a) below:

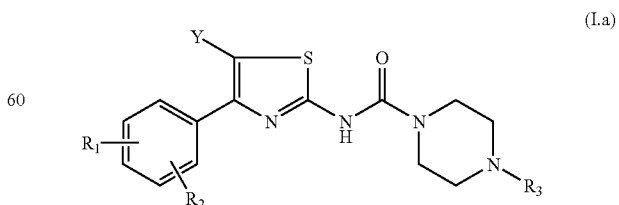

(I.a)

in which R$_1$, R$_2$, R$_3$ and Y are as defined above.

The compounds of the invention of formula (I.a) are those in which $R_1$ is in the 2-position and $R_2$ is in the 5-position of the phenyl group.

The compounds of the invention which may be cited include those in which:

$R_1$ represents an —O—$(C_1$-$C_8)$alkyl group; and/or $R_2$ represents a $(C_1$-$C_8)$alkyl, $(C_3$-$C_{10})$cycloalkyl, perfluoro$(C_1$-$C_4)$alkyl or —O—$(C_1$-$C_8)$alkyl group.

A sub-group of these compounds which may be cited includes those in which:

$R_1$ represents an —O—$(C_1$-$C_8)$alkyl group; and/or $R_2$ represents a $(C_1$-$C_8)$alkyl, $(C_3$-$C_{10})$cycloalkyl or —O—$(C_1$-$C_8)$alkyl group.

The compounds of the invention which may be cited are included in a first group of compounds of formula (I) or (I.a) wherein $R_3$ represents a group of formula —$(CH_2)_a$-A in which a represents 1, 2, 3 or 4, and A is selected from the group constituted by:

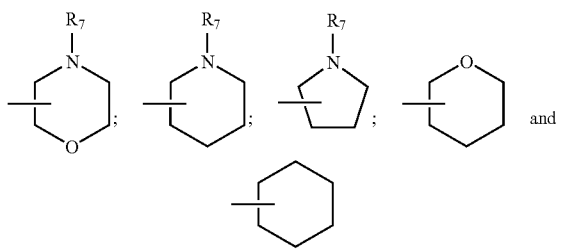

in which $R_7$, $R_1$, $R_2$, Y and p are as defined above.

The compounds of the invention which may be cited include a second group of compounds of general formula (I) or (I.a) in which $R_3$ represents a group of formula —CO$(CH_2)_b$-A in which b represents 0, 1, 2, 3 or 4, and A is selected from the group constituted by:

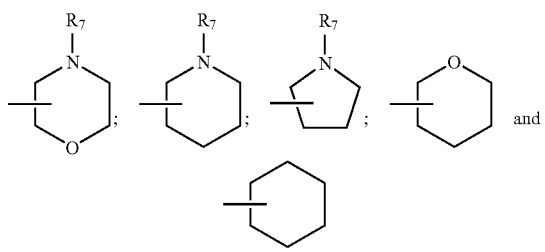

in which $R_7$, $R_1$, $R_2$, Y and p are as defined above.

The compounds of the invention cited above in the first group and in the second group which may be cited include a sub-group of compounds wherein A is selected from the group constituted by:

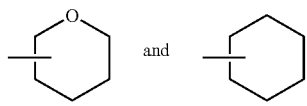

in which $R_1$, $R_2$, Y and p are as defined above.

The compounds of the invention which may be cited include a third group of compounds of general formula (I) or (I.a) wherein $R_3$ represents a group —B wherein B is selected from the group constituted by:

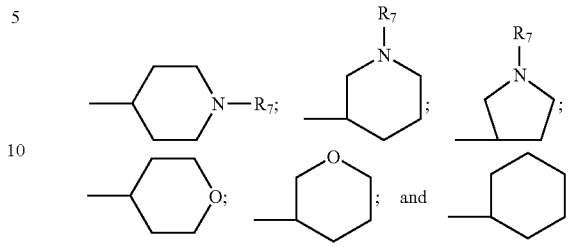

in which $R_7$, $R_1$, $R_2$, Y and p are as defined above.

Included in the compounds of the invention cited above, a first sub-group of compounds may be cited wherein $R_7$ is selected from the group constituted by —$(C_1$-$C_8)$alkyl-COO—$(C_1$-$C_8)$alkyl, —CO—$(C_1$-$C_8)$alkyl in which the alkyl is substituted with at least one halogen atom, —$(C_3$-$C_{10})$cycloalkyl, phenyl, —$SO_2$—$(C_1$-$C_8)$alkyl in which the alkyl is substituted with at least one halogen atom, —$SO_2$-phenyl in which the phenyl is substituted with at least one —O—$(C_1$-$C_8)$alkyl group, —$SO_2$-heteroaryl in which the heteroaryl is a pyrazole or an isoxazole or an imidazole and in which it is independently substituted with at least one group selected from halogen or —$(C_1$-$C_8)$alkyl, —$SO_2$—$N((C_1$-$C_8)$alkyl$)_2$, —$SO_2$—OH, —CO—$NH((C_1$-$C_8)$alkyl), —$(C_1$-$C_8)$alkyl-CN, —$(C_1$-$C_8)$alkyl-COOH, —$(C_1$-$C_8)$alkyl-COO$^-$M$^+$, —$(C_1$-$C_8)$alkyl-OH, —$(C_1$-$C_8)$alkyltetrazole, —$(C_1$-$C_8)$alkyl-CO—$NH_2$, in which M$^+$ is an alkali metal cation selected from Li$^+$, Na$^+$ and K$^+$, and when two alkyl or cycloalkyl substituents are bonded to a nitrogen atom, they may be independently identical or different, as well as a second sub-group of compounds wherein $R_7$ represents —$SO_2$—$(C_3$-$C_{10})$cycloalkyl.

Included in the compounds of formula (I) of the invention cited above are the following particular compounds:

4-((S)-1-cyclopropylpiperidin-3-ylmethyl)piperazine-1-carboxylic acid [4-(5-cyclohexyl-2-methoxyphenyl)thiazol-2-yl]amide;

4-(1-isopropylcarbamoylpiperidin-3-yl)piperazine-1-carboxylic acid [4-(5-cyclohexyl-2-methoxyphenyl)thiazol-2-yl]amide;

4-(1-cyclopropanesulphonylpiperidin-4-yl)piperazine-1-carboxylic acid [4-(5-cyclohexyl-2-methoxyphenyl)thiazol-2-yl]amide;

the ethyl ester of 3-((R)-3-{4-[4-(5-cyclohexyl-2-methoxyphenyl)thiazol-2-ylcarbamoyl]piperazin-1-ylmethyl}piperidin-1-yl)propionic acid;

3-((R)-3-{4-[4-(5-cyclohexyl-2-methoxyphenyl)thiazol-2-ylcarbamoyl]piperazin-1-ylmethyl}piperidin-1-yl)propionic acid;

the ethyl ester of 4-((R)-3-{4-[4-(5-cyclohexyl-2-methoxyphenyl)thiazol-2-ylcarbamoyl]piperazin-1-ylmethyl}piperidin-1-yl)butyric acid;

4-((R)-3-{4-[4-(5-cyclohexyl-2-methoxyphenyl)thiazol-2-ylcarbamoyl]piperazin-1-ylmethyl}piperidin-1-yl)butyric acid;

the ethyl ester of 5-((R)-3-{4-[4-(5-cyclohexyl-2-methoxyphenyl)thiazol-2-ylcarbamoyl]piperazin-1-ylmethyl}piperidin-1-yl)pentanoic acid;

5-((R)-3-{4-[4-(5-cyclohexyl-2-methoxyphenyl)thiazol-2-ylcarbamoyl]piperazin-1-ylmethyl}piperidin-1-yl)pentanoic acid;

4-cyclohexylpiperazine-1-carboxylic acid [4-(5-cyclohexyl-2-methoxyphenyl)thiazol-2-yl]amide;

4-(tetrahydropyran-4-yl)piperazine-1-carboxylic acid [4-(5-cyclohexyl-2-methoxyphenyl)thiazol-2-yl]amide.

More particularly, the following compound can be cited: 4-(tetrahydropyran-4-yl)piperazine-1-carboxylic acid [4-(5-cyclohexyl-2-methoxyphenyl)thiazol-2-yl]amide.

Included in the compounds of formula (I) of the invention cited above are the following further particular compounds:

4-((S)-1-cyclopropylpiperidin-3-ylmethyl)piperazine-1-carboxylic acid [4-(5-cyclohexyl-2-methoxyphenyl)thiazol-2-yl]amide;

4-(tetrahydropyran-4-carbonyl)piperazine-1-carboxylic acid [4-(5-cyclohexyl-2-methoxyphenyl)thiazol-2-yl]amide;

4-((S)-1-carbamoylmethylpiperidin-3-ylmethyl)piperazine-1-carboxylic acid [4-(5-cyclohexyl-2-methoxyphenyl)thiazol-2-yl]amide;

((S)-3-{4-[4-(5-cyclohexyl-2-methoxyphenyl)thiazol-2-ylcarbamoyl]piperazin-1-ylmethyl}piperidin-1-yl)acetic acid;

4-((S)-1-cyclopropylpiperidin-3-ylmethyl)piperazine-1-carboxylic acid [4-(5-cyclohexyl-2-methoxyphenyl)-5-fluorothiazol-2-yl]amide;

4-(tetrahydropyran-4-ylmethyl)piperazine-1-carboxylic acid [4-(5-cyclohexyl-2-methoxyphenyl)thiazol-2-yl]amide;

the ethyl ester of ((S)-3-{4-[4-(5-cyclohexyl-2-methoxyphenyl)thiazol-2-ylcarbamoyl]piperazin-1-ylmethyl}piperidin-1-yl)acetic acid;

4-[(R)-1-(2-cyanoethyl)piperidin-3-ylmethyl]piperazine-1-carboxylic acid [4-(5-cyclohexyl-2-methoxyphenyl)thiazol-2-yl]amide;

the sodium salt of 3-((R)-3-{4-[4-(5-cyclohexyl-2-methoxyphenyl)thiazol-2-ylcarbamoyl]piperazin-1-ylmethyl}piperidin-1-yl)propionic acid;

4-[(R)-1-(2-carbamoylethyl)piperidin-3-ylmethyl]piperazine-1-carboxylic acid [4-(5-cyclohexyl-2-methoxyphenyl)thiazol-2-yl]amide;

4-((R)-1-cyclopropylpiperidine-3-carbonyl)piperazine-1-carboxylic acid [4-(5-cyclohexyl-2-methoxyphenyl)thiazol-2-yl]amide;

4-((S)-1-cyclopropylpiperidin-3-ylmethyl)piperazine-1-carboxylic acid [4-(5-butyl-2-ethoxyphenyl)thiazol-2-yl]amide;

4-((S)-1-cyclopropylpiperidin-3-ylmethyl)piperazine-1-carboxylic acid [4-(5-cyclopentyl-2-ethoxyphenyl)thiazol-2-yl]amide;

4-((S)-1-cyclopropylpiperidin-3-ylmethyl)piperazine-1-carboxylic acid [4-(5-butyl-2-methoxyphenyl)thiazol-2-yl]amide;

4-((S)-1-cyanomethylpiperidin-3-ylmethyl)piperazine-1-carboxylic acid [4-(5-cyclohexyl-2-methoxyphenyl)thiazol-2-yl]amide;

4-((R)-1-cyclopropylpiperidin-3-yl)piperazine-1-carboxylic acid [4-(5-cyclohexyl-2-methoxyphenyl)thiazol-2-yl]amide;

4-(1-cyclopropylpiperidin-4-yl)piperazine-1-carboxylic acid [4-(5-cyclohexyl-2-methoxyphenyl)thiazol-2-yl]amide;

4-((S)-1-cyclopropanesulphonylpiperidin-3-ylmethyl)piperazine-1-carboxylic acid [4-(5-cyclohexyl-2-methoxyphenyl)thiazol-2-yl]amide;

4-((S)-1-phenylpiperidin-3-ylmethyl)piperazine-1-carboxylic acid [4-(5-cyclohexyl-2-methoxyphenyl)thiazol-2-yl]amide;

2-{4-[4-(5-cyclohexyl-2-methoxyphenyl)thiazol-2-ylcarbamoyl]piperazin-1-ylmethyl}piperidine-1-sulphonic acid;

4-[(S)-1-(2-hydroxyethyl)piperidin-3-ylmethyl]piperazine-1-carboxylic acid [4-(5-cyclohexyl-2-methoxyphenyl)thiazol-2-yl]amide;

4-[(S)-1-(2,2,2-trifluoroacetyl)piperidin-3-ylmethyl]piperazine-1-carboxylic acid [4-(5-cyclohexyl-2-methoxyphenyl)thiazol-2-yl]amide;

4-(tetrahydropyran-4-yl)piperazine-1-carboxylic acid [4-(5-cyclohexyl-2-methoxyphenyl)-5-fluorothiazol-2-yl]amide;

4-((S)-1-dimethylsulphamoylpiperidin-3-ylmethyl)piperazine-1-carboxylic acid [4-(5-cyclohexyl-2-methoxyphenyl)thiazol-2-yl]amide;

4-[(S)-1-(2H-tetrazol-5-ylmethyl)piperidin-3-ylmethyl]piperazine-1-carboxylic acid [4-(5-cyclohexyl-2-methoxyphenyl)thiazol-2-yl]amide;

4-[1-(5-chloro-1,3-dimethyl-1H-pyrazole-4-sulphonyl)piperidin-2-ylmethyl]piperazine-1-carboxylic acid [4-(5-cyclohexyl-2-methoxyphenyl)thiazol-2-yl]amide;

4-[1-(1,3-dimethyl-1H-pyrazole-4-sulphonyl)piperidin-2-ylmethyl]piperazine-1-carboxylic acid [4-(5-cyclohexyl-2-methoxyphenyl)thiazol-2-yl]amide;

4-[1-(1,5-dimethyl-1H-pyrazole-4-sulphonyl)piperidin-2-ylmethyl]piperazine-1-carboxylic acid [4-(5-cyclohexyl-2-methoxyphenyl)thiazol-2-yl]amide;

4-[1-(1-methyl-1H-pyrazole-4-sulphonyl)piperidin-2-ylmethyl]piperazine-1-carboxylic acid [4-(5-cyclohexyl-2-methoxyphenyl)thiazol-2-yl]amide;

4-[1-(5-methylisoxazole-4-sulphonyl)piperidin-2-ylmethyl]piperazine-1-carboxylic acid [4-(5-cyclohexyl-2-methoxyphenyl)thiazol-2-yl]amide;

4-[1-(1-methyl-1H-imidazole-4-sulphonyl)piperidin-2-ylmethyl]piperazine-1-carboxylic acid [4-(5-cyclohexyl-2-methoxyphenyl)thiazol-2-yl]amide;

4-(1-dimethylsulphamoylpiperidin-2-ylmethyl)piperazine-1-carboxylic acid [4-(5-cyclohexyl-2-methoxyphenyl)thiazol-2-yl]amide;

4-[1-(2,2,2-trifluoroethanesulphonyl)piperidin-2-ylmethyl]piperazine-1-carboxylic acid [4-(5-cyclohexyl-2-methoxyphenyl)thiazol-2-yl]amide;

4-[1-(4-methoxybenzenesulphonyl)piperidin-2-ylmethyl]piperazine-1-carboxylic acid [4-(5-cyclohexyl-2-methoxyphenyl)thiazol-2-yl]amide;

4-(tetrahydropyran-4-yl)piperazine-1-carboxylic acid [4-(5-cyclopentyl-2-ethoxyphenyl)thiazol-2-yl]amide;

4-[1-(3,5-dimethylisoxazole-4-sulphonyl)piperidin-2-ylmethyl]piperazine-1-carboxylic acid [4-(5-cyclohexyl-2-methoxyphenyl)thiazol-2-yl]amide;

4-(tetrahydropyran-4-yl)piperazine-1-carboxylic acid [4-(5-butyl-2-ethoxyphenyl)thiazol-2-yl]amide;

4-[(S)-1-(1-methyl-1H-imidazole-4-sulphonyl)piperidin-3-ylmethyl]piperazine-1-carboxylic acid [4-(5-cyclohexyl-2-methoxyphenyl)thiazol-2-yl]amide;

4-(tetrahydropyran-4-yl)piperazine-1-carboxylic acid [4-(5-cyclohexyl-2-ethoxyphenyl)thiazol-2-yl]amide;

4-(tetrahydropyran-4-yl)piperazine-1-carboxylic acid [4-(5-cyclopentyl-2-methoxyphenyl)thiazol-2-yl]amide;

4-(tetrahydropyran-4-yl)piperazine-1-carboxylic acid [4-(5-butyl-2-methoxyphenyl)thiazol-2-yl]amide;

4-(tetrahydropyran-4-yl)piperazine-1-carboxylic acid [4-(2-methoxy-5-propoxyphenyl)thiazol-2-yl]amide;

4-(tetrahydropyran-4-yl)piperazine-1-carboxylic acid [4-(5-propyl-2-methoxyphenyl)thiazol-2-yl]amide;

4-(tetrahydropyran-4-yl)[1,4]diazepane-1-carboxylic acid [4-(5-cyclohexyl-2-methoxyphenyl)thiazol-2-yl]amide.

The compounds of the invention include a fourth group of compounds which may be cited of general formula (I) or (I.a)

wherein $R_3$ represents a group of formula —$(CH_2)_a$—C in which a represents 1, 2, 3 or 4, and C is selected from the group constituted by:

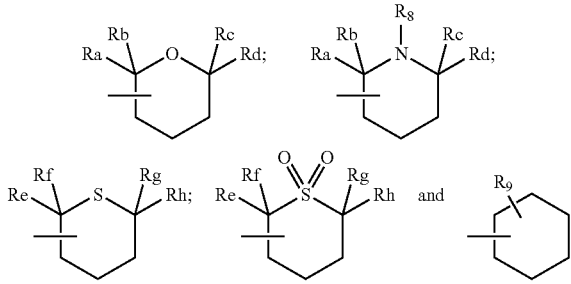

in which $R_8$, $R_9$, Ra, Rb, Rc, Rd, Re, Rf, Rg, Rh, $R_1$, $R_2$, Y and p are as defined above.

The compounds of the invention include a fifth group of compounds which may be cited of general formula (I) or (I.a) wherein $R_3$ represents a group of formula —$CO(CH_2)_b$—C in which b represents 0, 1, 2, 3 or 4, and C is selected from the group constituted by:

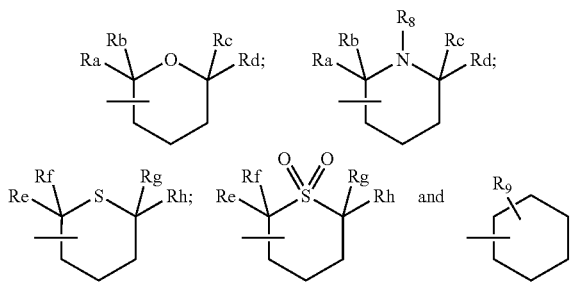

in which $R_8$, $R_9$, Ra, Rb, Rc, Rd, Re, Rf, Rg, Rh, $R_1$, $R_2$, Y and p are as defined above.

The compounds of the invention cited in the fourth group and in the fifth group include a first sub-group of compounds which may be cited wherein C is selected from the group constituted by:

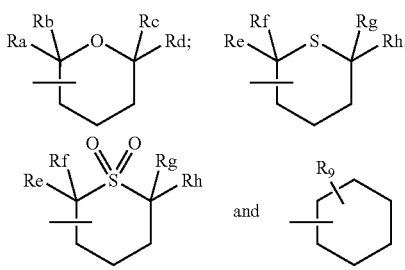

in which $R_9$, Ra, Rb, Rc, Rd, Re, Rf, Rg, Rh, $R_1$, $R_2$, Y and p are as defined above.

The compounds of the invention cited in the fourth group and in the fifth group include a second sub-group of compounds which may be cited wherein C represents:

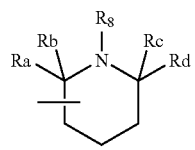

in which $R_8$, Ra, Rb, Rc, Rd, $R_1$, $R_2$, Y and p are as defined above.

The compounds of the invention include a sixth group of compounds which may be cited of general formula (I) or (I.a) in which $R_3$ represents a group -D wherein D is selected from the group constituted by:

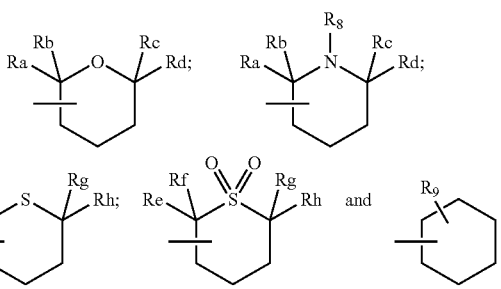

in which $R_8$, $R_9$, Ra, Rb, Rc, Rd, Re, Rf, Rg, Rh, $R_1$, $R_2$, Y and p are as defined above. In this sixth group, a sub-group of compounds may be cited in which $R_8$ is a hydrogen atom or a ($C_1$-$C_8$)alkyl group.

The compounds of formula (I) of the invention cited in the third, fourth and fifth groups and in their sub-groups which may be cited include the following particular compounds:
  4-(1,1-dioxohexahydro-1$\lambda^6$)-thiopyran-4-yl)piperazine-1-carboxylic acid [4-(5-cyclohexyl-2-methoxyphenyl)thiazol-2-yl]amide;
  4-(4-hydroxycyclohexyl)piperazine-1-carboxylic acid [4-(5-cyclohexyl-2-methoxyphenyl)thiazol-2-yl]amide;
  4-(1,2,2,6,6-pentamethylpiperidin-4-yl)piperazine-1-carboxylic acid [4-(5-cyclohexyl-2-methoxyphenyl)thiazol-2-yl]amide;
  4-(2,2,6,6-tetramethylpiperidin-4-yl)piperazine-1-carboxylic acid [4-(5-cyclohexyl-2-methoxyphenyl)thiazol-2-yl]amide;
  4-(2,2-dimethyltetrahydropyran-4-ylmethyl)piperazine-1-carboxylic acid [4-(5-cyclohexyl-2-methoxyphenyl)thiazol-2-yl]amide;
  4-(tetrahydrothiopyran-4-yl)piperazine-1-carboxylic acid [4-(5-cyclohexyl-2-methoxyphenyl)thiazol-2-yl]amide.

Certain intermediates which are of use in preparing compounds of formula (I) may also act as a final product of formula (I), as will become apparent from the examples given below.

In a similar manner, certain compounds of formula (I) of the invention may act as intermediates for use in preparing compounds of formula (I) according to the invention.

The term "protective group Gp" as used below means a group which can, on the one hand, protect a reactive function, such as a hydroxyl group or an amine group during a synthesis and, on the other, can regenerate the intact reactive function at the end of synthesis. Examples of protective groups and methods for protection and deprotection are given in "Protective Groups in Organic Synthesis", Green et al., 2$^{nd}$ Edition (John Wiley & Sons, Inc., New York).

The term "parting group X" as used below means a group which can easily be cleaved from a molecule by breaking a heterolytic bond, with departure of an electron pair. Said group may thus be readily replaced by another group during a substitution reaction, for example. Said parting groups are, for example, halogens or an activated hydroxyl group such as mesyl (methanesulphonyl), tosyl (toluenesulphonyl), triflate, acetate, etc. Examples of parting groups and references to their preparation are given in "Advances in Organic Chemistry", J. March, 3$^{rd}$ Edition, Wiley Interscience, p. 310-316.

The term "$R_1$, $R_2$ or $R_3$ precursor" as used below means a substituent $R'_1$, $R'_2$ or $R'_3$ which may be transformed into $R_1$, $R_2$ and $R_3$ by one or more chemical reactions.

The term "group Z" as used below means a leaving group of a functional derivative of a carboxylic acid such as an acid chloride, a mixed or symmetrical anhydride, or the appropriately activated acid, for example benzotriazol-1-yloxytris (dimethylamino) phosphonium hexafluorophosphate (BOP), O-benzotriazol-1-yl-N,N,N',N'-tetramethyluronium hexafluorophosphate (HBTU) or O-benzotriazol-1-yl-N,N,N',N'-tetramethyluronium tetrafluoroborate (TBTU).

When one or more substituents $R_{11}$, $R_{12}$ and/or $R'_3$ represent a group containing an amine or hydroxyl function, said functions may be protected in an intermediate manner: an amine function may be protected by an alkanoyl, benzyl, tert-butoxycarbonyl (Boc), benzyloxycarbonyl or 9-fluorenylmethoxycarbonyl (Fmoc) group, for example; a hydroxyl function may be protected in the ether or ester form, for example.

The compounds of the invention may be prepared using various methods described in the present patent application. In a first aspect, the present invention concerns processes for preparing products of formula (I) and the intermediate products thereof.

The compounds of formula (I) of the invention may be prepared in accordance with the following general scheme 1.

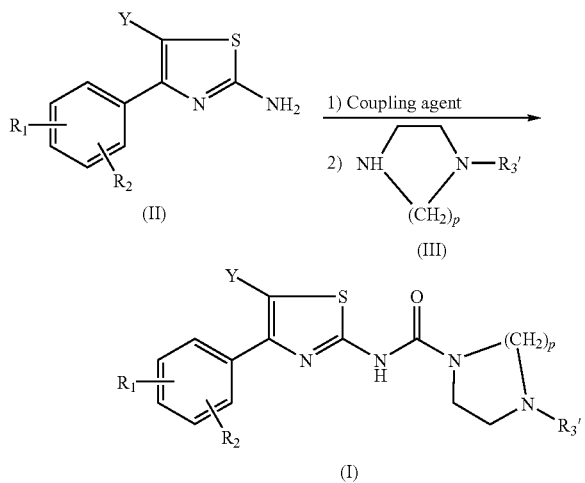

In accordance with scheme 1, the compounds of the invention are obtained by coupling an aminothiazole derivative of formula (II) wherein $R_1$, $R_2$, Y are as defined above with an amine derivative of formula (III) in which $R'_3$ represents a precursor group of $R_3$ or a group $R_3$ as defined above and p is as defined above.

The aminothiazole derivatives of formula (II) may be obtained using the methods described in patent application WO2004/096798.

In scheme 1, the aminothiazole derivative of formula (II) is brought into the presence of a coupling agent for a period of 2 to 16 hours, then with the amine derivative of formula (III) for a period of 0.5 to 4 hours.

The coupling agent may be selected from those which are known to the skilled person, for example phosgene, di-(N-succinimidyl)carbonate, 1,1'-carbonyl-diimidazole, using methods described in the "Encyclopedia of Reagents for Organic Synthesis", L. A. Paquette, volume 2, p 1006; volume 4, p 2304; volume 6, p 4107.

The reaction may be carried out in various solvents, for example dichloromethane, dimethylformamide, toluene, in the presence of a base such as triethylamine or $K_2CO_3$, at a temperature of 0° C. to 100° C.

The aminated derivatives of formula (III) are known or can be prepared using the methods described in particular in the document WO 87/01706 or using the methods described below. Groups A' and C' below respectively represent a precursor group of group A or C, or a group A or C as defined above.

The compounds of formula (III), in which $R'_3$ represents a precursor group of $R_3$ or a group $R_3$ as defined above and in which p is as defined above, are obtained from compounds of formula (IV) by deprotecting the nitrogen of the piperazine or the homo-piperazine protected using methods which are known to the skilled person or described in the literature (WO03/104230 and WO03/057145).

By way of example, the following procedure may be followed:

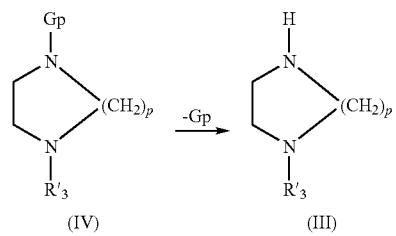

The compounds of formula (IV) are commercially available or may be synthesized from commercially available compounds using methods which are known to the skilled person. The compounds of formula (IV), wherein $R'_3$ represents a precursor group of the group $R_3$ in which $R_3$ represents a —$CO(CH_2)_b$-A or —$CO(CH_2)_b$—C group (compounds of formula (IV.2) or (IV.5)), may also be obtained using scheme 2 below:

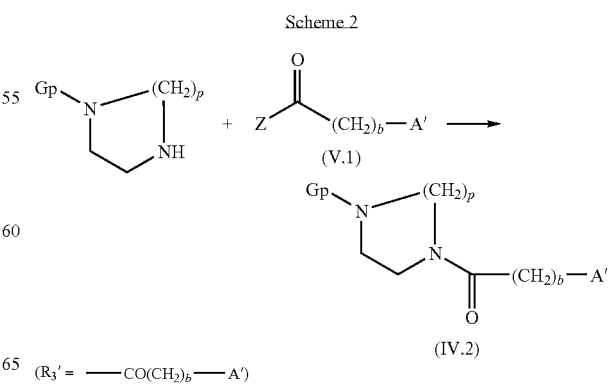

($R_3'$ = ——$CO(CH_2)_b$——A')

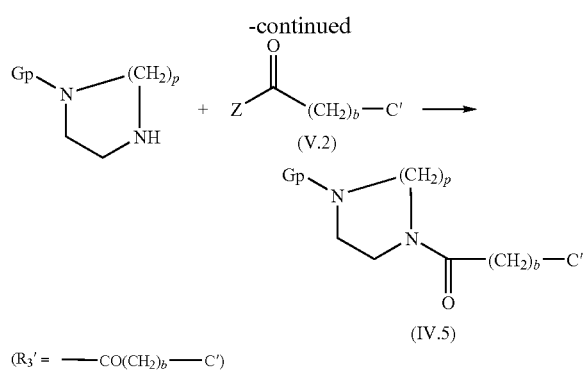

In scheme 2, a piperazine or a mono-protected homopiperazine (Gp=BOC or Gp=benzyl) reacts with a compound of formula (V.1) or (V.2) in which Z represents a leaving group, or a group derived from activation of a carboxylic acid function, to respectively give the compound of formula (IV.2) or (IV.5) by acylation or peptide type coupling in the presence of a base such as $K_2CO_3$, triethylamine, diisopropylthylamine or caesium carbonate, optionally in the presence of a coupling reagent such as BOP, TBTU or CDI, in a solvent such as THF, acetonitrile or DMF at temperatures of 0° C. to 150° C.

The compounds of formula (IV), wherein $R'_3$ represents a precursor group of the group $R_3$ in which $R_3$ represents a —$(CH_2)_a$-A or —$(CH_2)_a$—C group (compounds of formula (IV.1) or (IV.4)), may also be obtained using scheme 3 below:

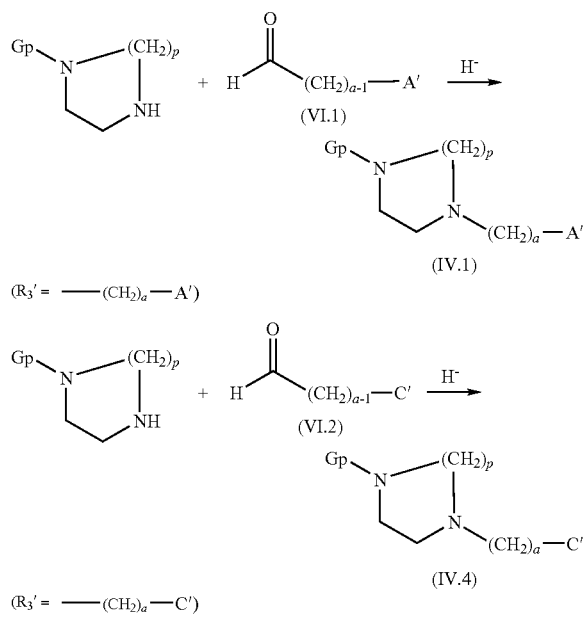

In this process, a piperazine or a mono-protected homopiperazine (Gp=BOC or Gp=benzyl) reacts with an aldehyde of formula (VI.1) or (VI.2) to respectively give the compound of formula (IV.1) or (IV.4) under reductive amination reaction conditions in the presence of a reducing agent such as NaHB(OAc)$_3$ or NaBH$_3$CN in a solvent such as 1,2-dichloroethane, dichloromethane, methanol or THF at temperatures of 0° C. to 70° C. (Synth. Commun., 1998, 28 (10), 1897-1905, J. Org. Chem., 1992, 57 (11), 3218-3225, J. Org. Chem., 1996, 61, 3849-3862, Tetrahedron Lett., 1990, 31, 5595-5598).

Alternatively, the compounds of formula (IV.1) and (IV.4) may be synthesized by a substitution reaction using the process illustrated in scheme 4 below:

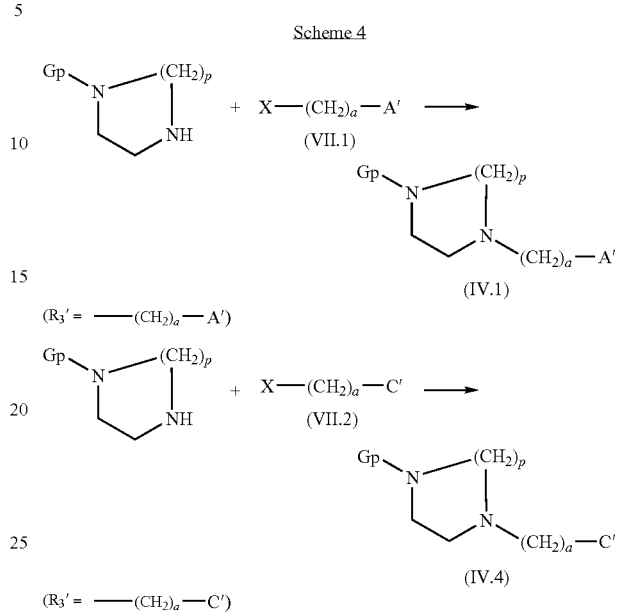

In scheme 4, a piperazine or a mono-protected homopiperazine (Gp=BOC or Gp=benzyl) reacts with a compound of formula (VII.1) or (VII.2) in which X represents a leaving group to respectively produce the compound of formula (IV.1) or (IV.4). The reaction is carried out without solvent or in a solvent such as tetrahydrofuran, dimethylformamide, toluene or acetonitrile in the presence or absence of a base such as triethylamine or $K_2CO_3$ at temperatures from ambient temperature to 200° C. for a period of 1 to 24 hours.

The compounds of formula (IV), wherein $R'_3$ represents a precursor group of the group $R_3$ in which $R_3$ represents a —B or -D group (compounds of formula (IV.3) or (IV.6)), may be prepared by reacting a piperazine or a mono-protected homopiperazine (Gp=BOC or Gp=benzyl) and a ketone precursor B' of B or a ketone precursor D' of D, by a reductive amination reaction in the presence of a reducing agent such as NaHB(OAc)$_3$, NaBH$_3$CN in a solvent such as 1,2-dichloroethane, methanol or dichloromethane, THF at temperatures of 0° C. to 70° C. using the following scheme:

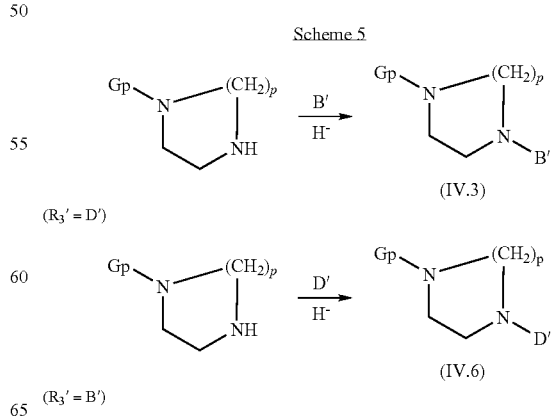

The ketones B' and D' used are commercially available or may be synthesized using the methods described in *Organic Process Research & Development*, 2004, 8, 939; *Synthesis*, 1989, 10, 767.

The compounds of formula (I) may also be prepared using scheme 6 below.

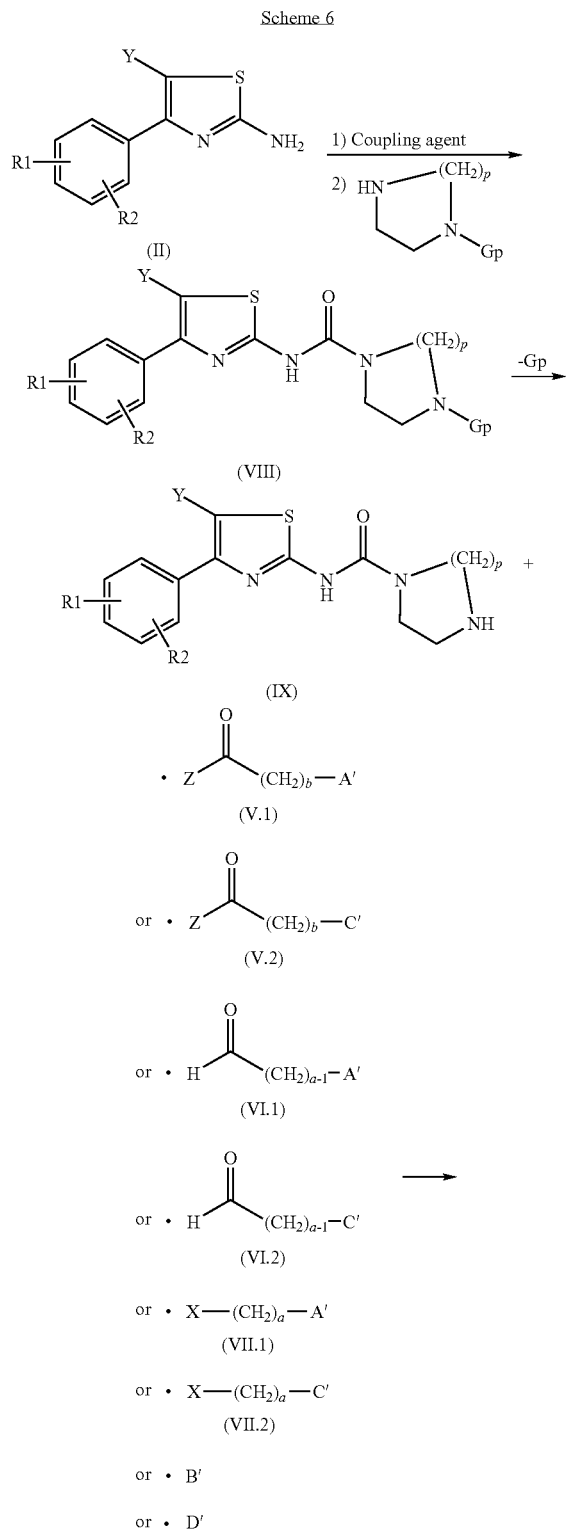

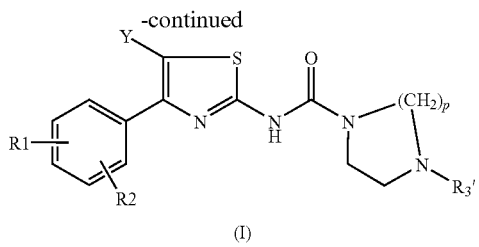

In scheme 6, the aminothiazole derivative of formula (II) as defined above is coupled to a piperazine or a mono-protected homo-piperazine (Gp=BOC or Gp=benzyl) to produce the compound of formula (VIII).

The reaction is carried out under the conditions described above given for scheme 1.

The compound of formula (VIII) is then deprotected to produce the compound of formula (IX), using methods which are known to the skilled person, which is reacted with a compound of formula (V.1), (V.2), (VI.1), (VI.2), (VII.1) or (VII.2), or with a ketone of formula B' or of formula D' as defined above. This reaction is carried out in accordance with the processes described above for synthesizing intermediates of formula (IV).

In the general synthesis schemes, when the mode of preparation thereof has not been described, this means that the starting compounds and the reagents are commercially available or have been described in the literature, or they may be prepared using the methods described here or which are known to the skilled person.

The following examples describe the preparation of compounds in accordance with the invention. The numbers of the compounds refer to those given in Table I, which shows the chemical structures of some compounds according to the invention.

In the preparations and examples below:
CyHex=a cyclohexyl group;
DSC=di-(N-succinimidyl)carbonate;
CDI=1,1'-carbonyldiimidazole;
DCE=dichloroethane;
TBME=tert-butyl methyl ether;
AT=ambient temperature;
DCM=dichloromethane;
DIPEA=diisopropylthylamine;
THF=tetrahydrofuran;
BOP=benzotriazol-1-yloxy-tris(dimethylamino)phosphonium hexafluorophosphate;
DMF=dimethylformamide;
Boc=tert-butyloxycarbonyl;
TFA=trifluoroacetic acid;
TBTU=2-(1H-benzotriazol-1-yl)-1,1,3,3-tetramethyluroniumtetrafluoroborate;
HOBT=hydroxybenzotriazole;
BSA=bis(trimethylsilyl)acetamide;
EtOAc=ethyl acetate;
AcCl=acetyl chloride;
MP=Melting Point (in degrees Celsius) measured using a Büchi B545 apparatus with a temperature gradient of 1° C. per minute;
MH+=molecular mass of the form of the molecule ionized by a proton.

The compounds were analyzed by coupled HPLC-UV-MS (liquid chromatography-UV detection-mass spectrometry). The apparatus used, sold by Agilent, was composed of a HP1100 chromatograph provided with an Agilent diode array detector and a MSD Quad quadripolar mass spectrometer.

The following analytical conditions were employed:
Column; Symmetry C18(50 ×2.1 mm; 3.5 µm )
Eluent A: $H_2O$ +TFA 0.005% at a pH of 3.15
Eluent B: $CH_3$ CN +TFA 0.005%

| Gradient: Time (min) | % B |
|---|---|
| 0 | 0 |
| 10 | 90 |
| 15 | 90 |
| 16 | 0 |
| 20 | 0 |

Column temperature: 30° C.
Flow rate: 0.4 ml/min
Detection: λ = 220 nm

Where "method B" is indicated in Table 1, the compounds were analyzed by LCMS under the following conditions: YMC Jsphere column (33×2.1 mm, 4 µm, eluent: $CH_3CN$+ 0.05% TFA: $H_2O$+0.05% TFA, gradient: 5:95 (0 min), then 95:5 (2.5 min), then 95:5 (3 min), flow rate: 1.3 mL/min, temperature: 30° C.
rt=retention time.
NMR=nuclear magnetic resonance, carried out with a Bruker Avance 200 (200 MHz) spectrometer. The solvent used was deuterated DMSO and the chemical displacements were expressed with respect to TMS. The following abbreviations were used:
s=singlet,
d=doublet,
d.d=double doublet,
t=triplet,
m=multiplet,
sel=broad singlet.
Optical purity was analyzed by HPLC on a Chiralpak AD (250 mm×4.6) column eluted with a $CO_2$/MeOH (80/20) mixture at 30° C. at a flow rate of 3 ml/min, P=20 MPa. The compounds were detected at 220 nm.
$α_D$=rotatory power. The rotatory powers were determined using a Perkin-Elmer 241-MC polarimeter for the sodium D line (λ=589 nm); the concentrations were expressed as 10 mg/ml; the measurements were carried out at ambient temperature.

EXAMPLE 1

4-((S)-1-cyclopropylpiperidin-3-ylmethyl)piperazine-1-carboxylic acid [4-(5-cyclohexyl-2-methoxyphenyl)thiazol-2-yl]amide (Compound No 1)

1.1. Preparation of the tert-butyl ester of (R)-3-((methylsulphonyloxy)methyl)piperidine-1-carboxylic acid 2.16 ml of methanesulphonyl chloride followed by 3.86 ml of triethylamine were added to a solution of 5 g of the tert-butyl ester of (R)-3-(hydroxymethyl)piperidine-1-carboxylic acid in 80 ml of DCM cooled to 0° C. The medium was stirred for 1 h 30 minutes at 0° C. then 0.7 ml of triethylamine and 0.54 ml of methanesulphonyl chloride were added. After 30 minutes at 0° C., the medium was hydrolysed, the organic phase was washed twice with water then with a saturated NaCl solution and then dried over $MgSO_4$. The medium was evaporated off to produce 6.8 g of a pale yellow oil.

1.2. Preparation of the tert-butyl ester of (S)-3-((4-benzylpiperazin-1-yl)methyl)piperidine-1-carboxylic acid The unrefined product obtained in step 1.1 was dissolved in 75 ml of toluene. 12.16 g of benzylpiperazine were added, the reaction medium was sealed off and heated for 5 hours at 150° C. After returning to AT, the medium was diluted in an ether/pentane (1/1) mixture, washed twice with a saturated $NaHCO_3$ solution, twice in water then with a saturated NaCl solution. After drying over $MgSO_4$ and evaporating, the unrefined product was purified by silica gel flash chromatography to produce 5.73 g of the expected solid.
MH+=374.3 at t=5.26 min 1.3. Preparation of the tert-butyl ester of (S)-3-(piperazin-1-ylmethyl)piperidine-1-carboxylic acid A solution of 4.0 g of the compound obtained in step 1.2 in 30 ml of methanol was hydrogenated in a closed reactor with microwave irradiation at 80° C. for 10 minutes in the presence of 1.7 g of Pd/C, 10% moisture, and 2.02 g of ammonium formate. The medium was filtered then evaporated to produce 2.89 g of a colourless oil.

1.4 Preparation of the tert-butyl ester of (S)-3-((4-(4-(5-cyclohexyl-2-methoxyphenyl)thiazol-2-ylcarbamoyl)piperazin-1-yl)methyl)piperidine-1-carboxylic acid 2.59 g of DSC were added to a solution of 2.78 g of 4-(5-cyclohexyl-2-methoxyphenyl)thiazol-2-amine, a compound described in patent application WO2004/096798, in 7 ml of dichloromethane and the medium was stirred for 12 hours at AT. 2.59 g of the compound described in step 1.3 were added and the medium was stirred for 3 hours at AT. The medium was hydrolysed with a solution of saturated $NaHCO_3$ then extracted into DCM. The organic phase was washed with water then with a saturated NaCl solution. After drying over $MgSO_4$, the solution was concentrated and purified by silica gel flash chromatography to produce 4.0 g of the expected compound in the form of a white solid.
MH+=598.7 at t=8.26 min 1.5 Preparation of 4-((R)-1-piperidin-3-ylmethyl)piperazine-1-carboxylic acid [4-(5-cyclohexyl-2-methoxyphenyl)thiazol-2-yl]amide 42 ml of a 4 M HCl solution in dioxane were added to a solution of 4 g of the compound obtained in step 1.4 in 10 ml of dioxane. The medium was stirred for 4 h at AT. The medium was filtered, the solid was rinsed with ether then taken up in DCM and treated with 1 M sodium hydroxide. The organic phase was washed with water then with a saturated NaCl solution. After drying over $MgSO_4$, the solution was concentrated to produce 3.16 g of the desired compound.
MH+=498.7 at t=6.27 min 1.6 Preparation of 4-((S)-1-cyclopropylpiperidin-3-ylmethyl)piperazine-1-carboxylic acid [4-(5-cyclohexyl-2-methoxyphenyl)thiazol-2-yl]amide 0.35 g of (1-ethoxycyclopropoxy)trimethylsilane then 0.05 g of $NaBH_3CN$ and 0.24 g of acetic acid were added to a solution of 0.2 g of the compound described in step 1.5 in 5 ml of MeOH. The medium was stirred for 2 h at 60° C. The medium was concentrated then taken up in EtOAc. The organic phase was washed twice with a saturated NaHCO$_3$ solution then with a saturated NaCl solution. After drying over MgSO$_4$, the organic phase was concentrated then purified by flash chromatography to produce 0.16 g of the expected product.

MP=88° C.

$\alpha_D$=+4°(c=1, MeOH)

EXAMPLE 2

[4-(1-isopropylcarbamoylpiperidin-3-yl)piperazine-1-carboxylic acid 4-(5-cyclohexyl-2-methoxyphenyl)thiazol-2-yl]amide (Compound No 2)

2.1. Preparation of the tert-butyl ester of 4-(1-benzylpiperidin-3-yl)piperazine-1-carboxylic acid 20 ml of a 10% sodium hydroxide solution were added to a suspension of 9.96 g of the hydrate of 1-benzylpiperidin-3-one mono-hydrochloride in suspension in 200 ml of DCM. The medium was stirred, the organic phase was decanted then washed with a saturated NaCl solution. After drying over MgSO$_4$, the organic phase was concentrated. The gum obtained was taken up in 180 ml of DCE, 10.1 g of Boc-piperazine was added followed by 15.9 g of NaBH(OAc)$_3$ and the medium was stirred for 12 h at AT. The medium was concentrated then taken up in EtOAc. The organic phase was washed twice with a saturated NaHCO$_3$ solution then with a saturated NaCl solution. After drying over MgSO$_4$, the organic phase was concentrated to produce 18.63 g of the expected product.

MP=103° C.

2.2. Preparation of 1-(1-benzylpiperidin-3-yl)piperazine 30 g of TFA were added to a solution of 9.2 g of the compound obtained in step 2.1 in 85 ml of DCM. The medium was stirred for 5 h then concentrated. The unrefined product obtained was taken up in DCM then washed 4 times with a 2 M sodium hydroxide solution. The organic phase was washed with a saturated NaCl solution. After drying over MgSO$_4$, the organic phase was concentrated to produce 6.32 g of the expected product.

NMR $^1$H: δ (ppm)=7.28 (sel, 5H), 3.43 (sel, 2H), 2.88 (d, 1H), 2.70 (d, 1H), 2.64 (m, 4H), 2.43-2.22 (m, 5H), 1.85-1.58 (m, 4H), 1.39 (ddd, 1H), 1.15 (ddd, 1H).

2.3. Preparation of 4-(1-benzyl-piperidin-3-yl)piperazine-1-carboxylic acid [4-(5-cyclohexyl-2-methoxyphenyl)thiazol-2-yl]amide The procedure was identical to that described in Example 1, starting from 4-(5-cyclohexyl-2-methoxyphenyl)thiazol-2-amine described in patent application WO2004/096798 and the compound obtained in step 2.2.

MP=90° C.

2.4. Preparation of 4-piperidin-3-ylpiperazine-1-carboxylic acid [4-(5-cyclohexyl-2-methoxyphenyl)thiazol-2-yl]amide 1.26 g of chloroethylchloroformate were added to a solution of 1.69 g of the compound obtained in step 2.3 in 10 ml of DCE at 0° C. The medium was brought to AT then heated under reflux for 45 min. The medium was evaporated off then taken up in 10 ml of MeOH and heated for 1 h under reflux. The unrefined product was filtered, the solid was rinsed with ether then dried to produce 1.27 g of the expected compound in the form of a trihydrochloride.

MP=240° C.

MH+=484.7 at 6.81 min 2.5. Preparation of 4-(1-isopropylcarbamoylpiperidin-3-yl)piperazine-1-carboxylic acid [4-(5-cyclohexyl-2-methoxyphenyl)thiazol-2-yl]amide 0.06 ml of isopropyl isocyanate was added to a solution of 0.2 g of the compound obtained in step 2.4 in 1.2 ml of DCM, at 0° C. The medium was stirred for 2 h at 0° C. then hydrolysed with 5 ml of water and diluted with 10 ml of DCM. The organic phase was washed twice with a saturated NaHCO$_3$ solution then with a saturated NaCl solution. After drying over MgSO$_4$, the organic phase was concentrated then purified by flash chromatography to produce 0.16 g of the expected product.

MP=134° C.

MH+=568.7 at t=7.61 min

EXAMPLE 3

4-(1-cyclopropanesulphonylpiperidin-4-yl)piperazine-1-carboxylic acid [4-(5-cyclohexyl-2-methoxyphenyl)thiazol-2-yl]amide (Compound No 3)

3.1 Preparation of 4-(1-benzylpiperidin-4-yl)piperazine-1-carboxylic acid [4-(5-cyclohexyl-2-methoxyphenyl)thiazol-2-yl]amide The procedure was identical to that described in Example 1, starting from 4-(5-cyclohexyl-2-methoxyphenyl)thiazol-2-amine, described in patent application WO2004/096798, and from 1-(1-benzylpiperidin-4-yl)piperazine.

MP=81° C.

3.2. Preparation of 4-piperidin-4-ylpiperazine-1-carboxylic acid [4-(5-cyclohexyl-2-methoxyphenyl)thiazol-2-yl]amide 1.31 g of chloroethylchloroformate were added to a solution of 1.77 g of the compound obtained in step 3.1 in 10 ml of DCE, at 0° C. The medium was returned to AT then heated under reflux for 45 min. The medium was evaporated off then taken up in 10 ml of MeOH and heated for 1 h under reflux. The unrefined product was filtered, the solid was rinsed with ether then dried to produce 1.27 g of the expected compound in the form of a trihydrochloride.

MH+=484.6 at 6.21 min 3.3. Preparation of 4-(1-cyclopropanesulphonylpiperidin-4-yl)piperazine-1-carboxylic acid [4-(5-cyclohexyl-2-methoxyphenyl)thiazol-2-yl]amide 0.04 ml of cyclopropylsulphonyl chloride then 0.06 ml of triethylamine were added to a solution of 0.2 g of the compound described in preparation 3.2 in DCM. The medium was stirred at AT for 4 h. The medium was diluted in DCM then hydrolysed with 5 ml of water. The organic phase was washed twice with a saturated NaHCO$_3$ solution then with a saturated NaCl solution. After drying over MgSO$_4$, the organic phase was concentrated then purified by flash chromatography to produce 0.18 g of the expected product.

MP=138° C.

MH+=588.8 at t=7.49 min

EXAMPLE 4

Ethyl ester of 3-((R)-3-{4-[4-(5-cyclohexyl-2-methoxy-phenyl)thiazol-2-ylcarbamoyl]piperazin-1-ylmethyl}piperidin-1-yl)propionic acid (Compound No 4)

0.08 ml of triethylamine then 0.05 ml of the ethyl ester of 3-bromopropionic acid were added to a solution of 0.2 g of the compound described in step 1.5 in 2 ml of toluene. The medium was stirred for 48 h at AT. The medium was diluted in ethyl ether then filtered. The filtrate was washed with water then with a saturated NaCl solution. After drying over MgSO$_4$, the organic phase was concentrated to produce 0.21 g of the expected product.

MH+=598.8 at t=6.84 min

EXAMPLE 5

3-((R)-3-{4-[4-(5-cyclohexyl-2-methoxyphenyl)thiazol-2-ylcarbamoyl]piperazin-1-ylmethyl}piperidin-1-yl)propionic acid (Compound No 5)

0.31 ml of 5 M sodium hydroxide was added to a solution of 0.208 g of the compound described in step 4 in 3 ml of methanol, at 0° C. The medium was stirred for 24 h at AT. The medium was concentrated then taken up in water. A 6N HCl solution was added dropwise until a precipitate appeared. The solid was extracted into DCM then, after drying over MgSO$_4$, the organic phase was concentrated to produce 0.15 g of the expected product.

MH+=570.7 at t=6.64 min
MP=144° C.

EXAMPLE 6

4-(tetrahydropyran-4-yl)piperazine-1-carboxylic acid [4-(5-cyclohexyl-2-methoxyphenyl)thiazol-2-yl]amide (Compound No 11)

This compound could be obtained using the process described in preparation 1.4 between 4-(5-cyclohexyl-2-methoxyphenyl)thiazol-2-amine and 1-(tetrahydro-2H-pyran-4-yl)piperazine described in J. Med. Chem.; EN; 47; 11; 2004; 2833-2838.

Synthesis may be carried out by another method:

6.1 Preparation of the tert-butyl ester of 4-[4-(5-cyclohexyl-2-methoxyphenyl)thiazol-2-ylcarbamoyl]piperazine-1-carboxylic acid 2.9 g of DSC were added to a solution of 3.0 g of 4-(5-cyclohexyl-2-methoxyphenyl)thiazol-2-amine, a compound described in patent application WO2004/096798, in 100 ml of dichloroethane; the medium was stirred for 16 hours at AT. 2.0 g of BOC-piperazine were added and the medium was stirred for 3 hours at AT. The medium was hydrolysed with a saturated NaHCO$_3$ solution then extracted into DCM. The organic phase was washed with water then with a saturated NaCl solution. After drying over MgSO$_4$, the solution was concentrated and purified by silica gel flash chromatography to produce 5.1 g of the expected compound in the form of a beige solid.

MH+=501.7 at t=11.72 min

6.2 Preparation of piperazine-1-carboxylic acid [4-(5-cyclohexyl-2-methoxyphenyl)thiazol-2-yl]amide 19 ml of a 4 M HCl solution in dioxane were added dropwise to a solution of 5.1 g of the compound obtained in step 6.1 in 100 ml of dioxane. The medium was stirred for 4 hours at AT. The medium was filtered, the solid was rinsed with ether then dried to produce 4.38 g of a white powder. The solid was taken up in DCM and treated with 1 M sodium hydroxide. The organic phase was washed with water then with a saturated NaCl solution. After drying over MgSO$_4$, the solution was concentrated to produce 3.7 g of the expected compound.

MH+=401.6 at t=7.19 min

6.3 Preparation of 4-(tetrahydropyran-4-yl)piperazine-1-carboxylic acid [4-(5-cyclohexyl-2-methoxyphenyl)thiazol-2-yl]amide 0.4 g of dihydro-2H-pyran-4(3H)-one then 1.59 g of NaBH(OAc)$_3$ were added to a solution of 1.4 g of the piperazine obtained in step 6.2 in 13 ml of dichloroethane, and the medium was stirred for 72 hours at AT. The medium was concentrated then taken up in DCM. The organic phase was washed twice with a saturated NaHCO$_3$ solution then with a saturated NaCl solution. After drying over MgSO$_4$, the organic phase was concentrated to produce 1.7 g of the expected product.

The beige powder obtained was purified by silica gel flash chromatography to produce 1.42 g of the expected compound in the form of a white solid.

MH+=484.7 at t=7.42 min
MP=226° C.

EXAMPLE 7

4-(tetrahydropyran-4-carbonyl)piperazine-1-carboxylic acid [4-(5-cyclohexyl-2-methoxyphenyl)thiazol-2-yl]amide (Compound No 13)

122 mg of TBTU, 26 mg of HOBt and 0.17 ml of DIPEA were added to a solution of 41 mg of tetrahydro-2H-pyran-4-carboxylic in 0.7 ml of DCM, at AT. The medium was stirred at AT for 1 hour 15 minutes then 100 mg of the compound described in step 6.2 were added. The medium was stirred for 12 hours at AT. The medium was taken up in DCM, washed three times in a saturated Na$_2$CO$_3$ solution then with a saturated NaCl solution. After drying over MgSO$_4$ and evaporation, 0.21 g of the unrefined product was purified by silica gel flash chromatography to produce 0.08 g of the expected compound in the form of a white solid.

MH+=513.7 at t=9.88 min
MP=276° C.

EXAMPLE 8

4-(tetrahydropyran-4-ylmethyl)piperazine-1-carboxylic acid [4-(5-cyclohexyl-2-methoxyphenyl)thiazol-2-yl]amide (Compound No 17)

0.044 g of tetrahydro-2H-pyran-4-carbaldehyde was added to a solution of 0.155 g of the piperazine obtained in step 6.2 in 1.5 ml of dichloroethane followed, after stirring for 1 hour at AT, by 0.114 g of NaBH(OAc)$_3$, and the medium was stirred for 12 hours at AT. The medium was diluted in DCM. The organic phase was washed twice with a saturated NaHCO$_3$ solution then with a saturated NaCl solution. After drying over MgSO$_4$, the organic phase was concentrated to produce 0.16 g of unrefined product. The solid was purified by silica gel flash chromatography to produce 0.12 g of the expected compound in the form of a white solid.

MH+=499.7 at t=7.75 min
MP=114° C.

EXAMPLE 9

4-((S)-1-carbamoylmethylpiperidin-3-ylmethyl)piperazine-1-carboxylic acid [4-(5-cyclohexyl-2-methoxyphenyl)thiazol-2-yl]amide (Compound No 14)

9.1 Preparation of the ethyl ester of ((S)-3-{4-[4-(5-cyclohexyl-2-methoxyphenyl)thiazol-2-ylcarbamoyl]piperazin-1-ylmethyl}piperidin-1-yl)acetic acid (Compound No 18)

This compound was synthesized starting from the compound described in preparation 1.5 and from ethyl 2-bromoacetate using an identical process to that described in preparation 4.

9.2 Preparation of ((S)-3-{4-[4-(5-cyclohexyl-2-methoxyphenyl)thiazol-2-ylcarbamoyl]-piperazin-1-ylmethyl}piperidin-1-yl)acetic acid (Compound No 15)

This compound was synthesized from the compound described in preparation 9.1 using an identical process to that described in preparation 5.

9.3 Preparation of 4-((S)-1-carbamoylmethylpiperidin-3-ylmethyl)piperazine-1-carboxylic acid [4-(5-cyclohexyl-2-methoxyphenyl)thiazol-2-yl]amide 0.1 g of TBTU, 0.02 g of HOBt then 0.08 ml of DIPEA were added to a solution of 0.1 g of the compound described in step 9.2 in 1 ml of DCM. After stirring for 2 hours at AT, ammonia was bubbled into the solution for 2 hours. The reaction medium was filtered, the filtrate was washed with a saturated $NaHCO_3$ solution then with a saturated NaCl solution. After drying over $MgSO_4$, the organic phase was concentrated to produce 0.09 g of unrefined product. The unrefined product was purified by silica gel flash chromatography to produce 0.052 g of the expected compound in the form of a white solid.

MH+=555.7 at t=6.68 min
MP=134° C.

EXAMPLE 10

4-[(S)-1-(2H-tetrazol-5-ylmethyl)piperidin-3-ylmethyl]piperazine-1-carboxylic acid [4-(5-cyclohexyl-2-methoxyphenyl)thiazol-2-yl]amide (Compound No 42)

10.1 Preparation of 4-((S)-1-cyanomethylpiperidin-3-ylmethyl)piperazine-1-carboxylic acid [4-(5-cyclohexyl-2-methoxyphenyl)thiazol-2-yl]amide (Compound No 26)

0.1 g of $Na_2CO_3$ was added to a solution of 0.45 g of the compound obtained in step 1.5 in 4 ml of acetone. The medium was cooled to 0° C., then 0.06 ml of 2-chloroacetonitrile was added and the medium was stirred until it reached AT. 0.012 ml of 2-chloroacetonitrile and 0.02 g of $Na_2CO_3$ were added. The medium was stirred for 2 hours at AT then concentrated. The unrefined product was comminuted in water then extracted with ether. The organic phase was washed twice with a saturated $NaHCO_3$ solution then with a saturated NaCl solution. After drying over $MgSO_4$, the organic phase was concentrated then purified by silica gel flash chromatography to produce 0.34 g of the expected compound in the form of a white solid.

MH+=537.7 at t=7.67 min
MP=106° C.

10.2 Preparation of 4-[(S)-1-(2H-tetrazol-5-ylmethyl)piperidin-3-ylmethyl]piperazine-1-carboxylic acid [4-(5-cyclohexyl-2-methoxyphenyl)thiazol-2-yl]amide 0.06 g of $NaN_3$ and 0.14 g of $ZnBr_2$ were added to a suspension of 0.34 g of the compound synthesized in step 10.1 in a mixture of 3 ml of water and 1 ml of isopropanol. The mixture was heated to 80° C. for 40 hours, 0.03 g of $NaN_3$ and 0.07 g of $ZnBr_2$ were then added and stirring was maintained at 80° C. for 12 hours. The medium was filtered, the solid was rinsed with water then with ether. The solid was purified by preparative HPLC to produce 56 mg of the expected compound.

MH+=580.7 at t=7.32 min

EXAMPLE 11

4-((S)-1-phenylpiperidin-3-ylmethyl)piperazine-1-carboxylic acid [4-(5-cyclohexyl-2-methoxyphenyl)thiazol-2-yl]amide (Compound No 30)

11.1 Preparation of (R)-1-benzyl-4-(piperidin-3-ylmethyl)piperazine 20 ml of a 4 M HCl solution in dioxane were added to a solution of 1.35 g of the compound obtained in step 1.2 in 5 ml of dioxane. The medium was stirred for 2 h at AT. The medium was filtered, the solid was rinsed with ether then taken up in DCM and treated with 1 M sodium hydroxide. The organic phase was washed with water then with a saturated NaCl solution. After drying over $MgSO_4$, the solution was concentrated to produce 1 g of unrefined product.

MH+=274.3 at t=5.52 min

11.2 Preparation of (S)-1-benzyl-4-((1-phenylpiperidin-3-yl)methyl)piperazine 0.26 g of phenyl trifluoromethanesulphonate and 0.8 g of the amine prepared in step 11.1 in 5.6 ml of NMP were placed in a tube. The tube was heated under pressure in a microwave oven for 30 minutes at 230° C. After allowing to cool to AT, the medium was hydrolysed then extracted with ether. The organic phase was washed with water then with a saturated NaCl solution. After drying over $MgSO_4$, the solution was concentrated to produce 0.41 g of unrefined product. The solid was purified by silica gel flash chromatography to produce 0.067 g of the expected compound.

MH+=350.3 at t=9.97 min

11.3 Preparation of (S)-1-((1-phenylpiperidin-3-yl)methyl)piperazine 0.05 g of 50% Pd/C, 10% moisture, was added to a solution of 0.066 g of the compound obtained in step 11.2 in 9 ml of methanol. The medium was stirred at AT for 48 hours under 10 bar of hydrogen. After filtering over celite, the filtrate was evaporated off to produce 0.037 g of the desired compound.

11.4 Preparation of 4-((S)-1-phenylpiperidin-3-ylmethyl)piperazine-1-carboxylic acid [4-(5-cyclohexyl-2-methoxyphenyl)thiazol-2-yl]amide The procedure was identical to that described in Example 1, starting from 4-(5-cyclohexyl-2-methoxyphenyl)thiazol-2-amine, described in patent application WO2004/096798, and from the amine obtained in step 11.3.

MH+=574.8 at t=8.12 min

TABLE I
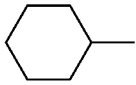
| Compound N° | R₁ | R₂ | R₃ | Y |
|---|---|---|---|---|
| 1 | —OCH₃ | 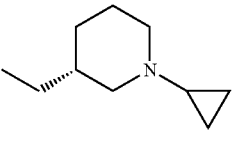 | 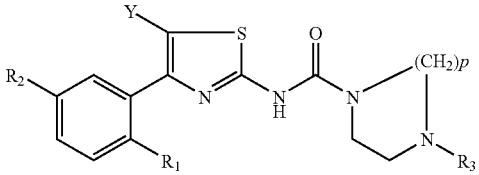 | H |
| 2 | —OCH₃ | 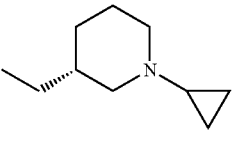 | 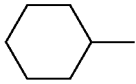 | H |
| 3 | —OCH₃ | 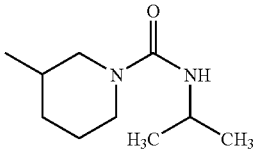 | 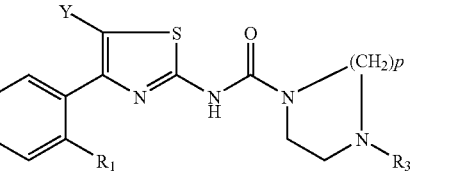 | H |
| 4 | —OCH₃ | 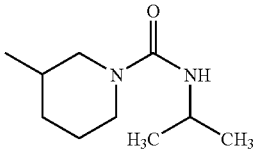 | 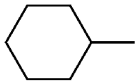 | H |
| 5 | —OCH₃ | 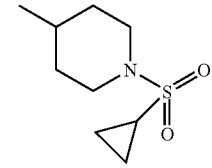 | 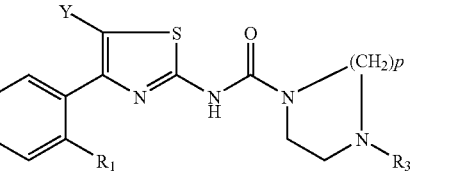 | H |
| 6 | —OCH₃ | 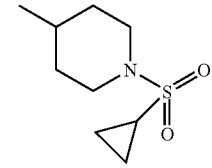 | 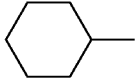 | H |
| 7 | —OCH₃ | 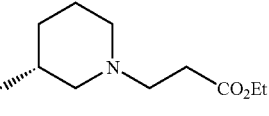 | 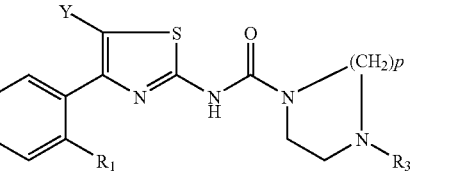 | H |
| 8 | —OCH₃ | 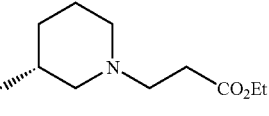 | 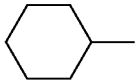 | H |
| 9 | —OCH₃ | 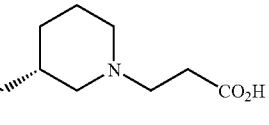 | 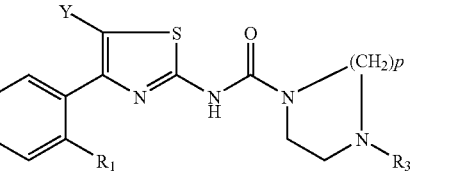 | H |
| 10 | —OCH₃ | 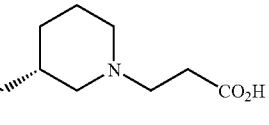 | 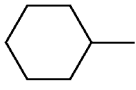 | H |

TABLE I-continued
| | | | | |
|---|---|---|---|---|
| 11 | —OCH₃ | 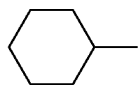 | 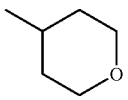 | H |
| 12 | —OCH₃ | 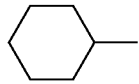 | 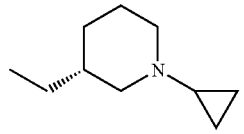 | H |
| 13 | —OCH₃ | 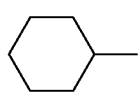 | 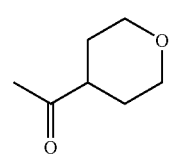 | H |
| 14 | —OCH₃ | 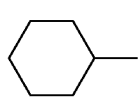 | 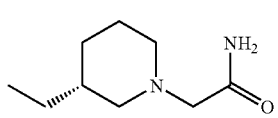 | H |
| 15 | —OCH₃ | 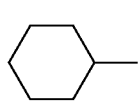 | 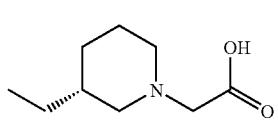 | H |
| 16 | —OCH₃ | 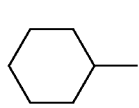 | 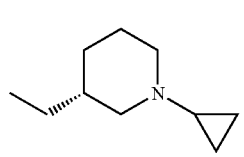 | F |
| 17 | —OCH₃ | 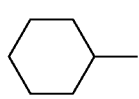 | 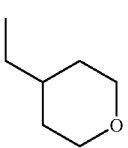 | H |
| 18 | —OCH₃ | 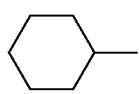 | 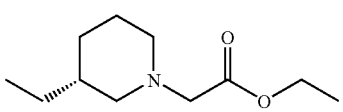 | H |
| 19 | —OCH₃ | 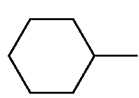 | 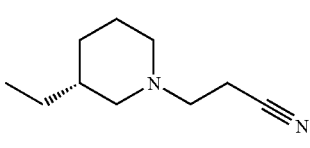 | H |
| 20 | —OCH₃ | 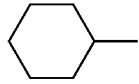 | 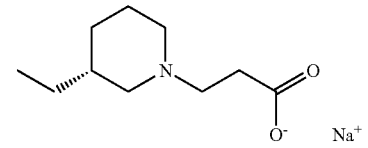 | H |
| 21 | —OCH₃ | 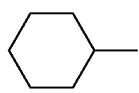 | 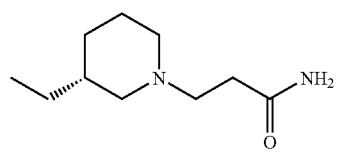 | H |

TABLE I-continued
| | | | | |
|---|---|---|---|---|
| 22 | —OCH₃ | 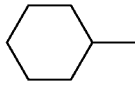 | 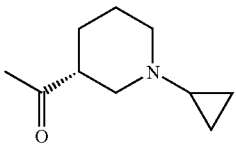 | H |
| 23 | —OCH₂—CH₃ | —(CH₂)₃—CH₃ | 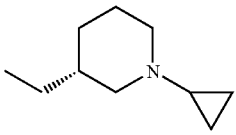 | H |
| 24 | —OCH₂—CH₃ | 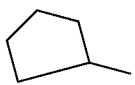 | 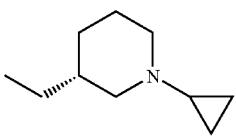 | H |
| 25 | —OCH₃ | —(CH₂)₃—CH₃ | 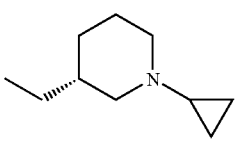 | H |
| 26 | —OCH₃ | 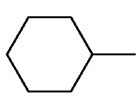 | 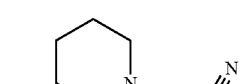 | H |
| 27 | —OCH₃ | 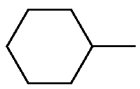 | 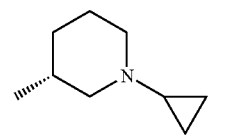 | H |
| 28 | —OCH₃ | 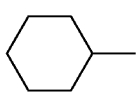 | 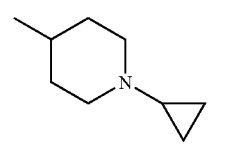 | H |
| 29 | —OCH₃ | 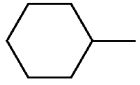 | 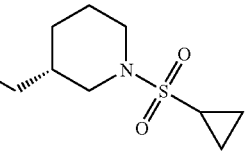 | H |
| 30 | —OCH₃ | 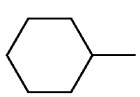 | 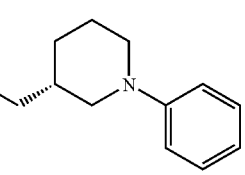 | H |
| 31 | —OCH₃ | 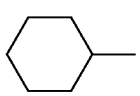 | 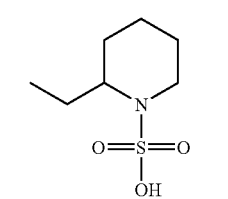 | H |

TABLE I-continued
| | | | | |
|---|---|---|---|---|
| 32 | —OCH₃ | 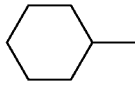 | 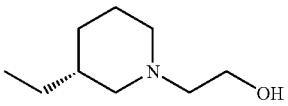 | H |
| 33 | —OCH₃ | 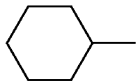 | 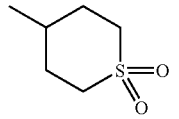 | H |
| 34 | —OCH₃ | 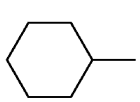 | 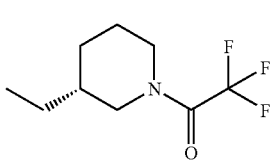 | H |
| 35 | —OCH₃ | 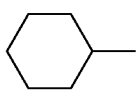 | 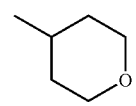 | F |
| 36 | —OCH₃ | 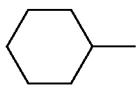 | 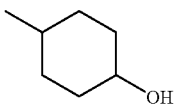 | H |
| 37 | —OCH₃ | 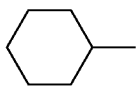 | 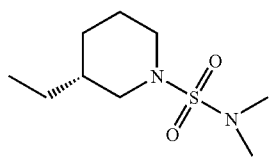 | H |
| 38 | —OCH₃ | 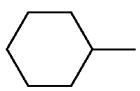 | 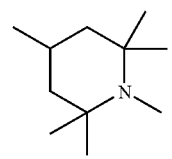 | H |
| 39 | —OCH₃ | 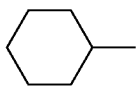 | 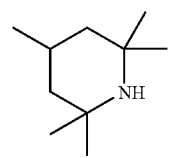 | H |
| 40 | —OCH₃ | 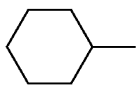 | 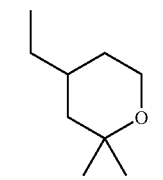 | H |
| 41 | —OCH₃ | 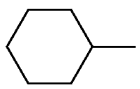 | 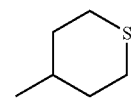 | H |
| 42 | —OCH₃ | 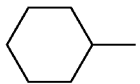 | 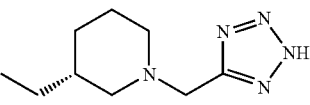 | H |

TABLE I-continued

| 43 | —OCH₃ | cyclohexyl- | 2-ethyl-1-(5-chloro-1,3-dimethyl-1H-pyrazol-4-ylsulfonyl)piperidine | H |
| 44 | —OCH₃ | cyclohexyl- | 2-ethyl-1-(1,3-dimethyl-1H-pyrazol-4-ylsulfonyl)piperidine | H |
| 45 | —OCH₃ | cyclohexyl- | 2-ethyl-1-(1,5-dimethyl-1H-pyrazol-4-ylsulfonyl)piperidine | H |
| 46 | —OCH₃ | cyclohexyl- | 2-ethyl-1-(1-methyl-1H-pyrazol-4-ylsulfonyl)piperidine | H |
| 47 | —OCH₃ | cyclohexyl- | 2-ethyl-1-(5-methylisoxazol-4-ylsulfonyl)piperidine | H |

TABLE I-continued
| 48 | —OCH₃ | 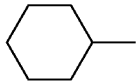 | 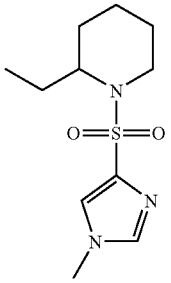 | H |
| --- | --- | --- | --- | --- |
| 49 | —OCH₃ | 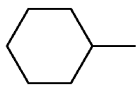 | 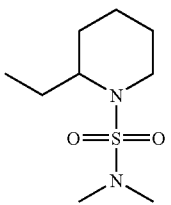 | H |
| 50 | —OCH₃ | 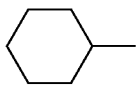 | 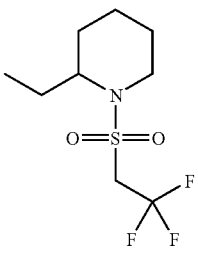 | H |
| 51 | —OCH₃ | 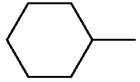 | 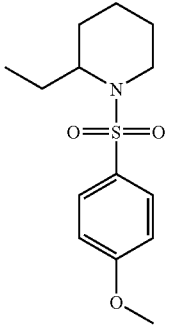 | H |
| 52 | —OCH₂—CH₃ | 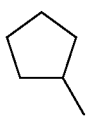 | 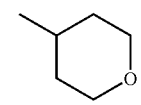 | H |
| 53 | —OCH₃ | 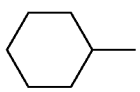 | 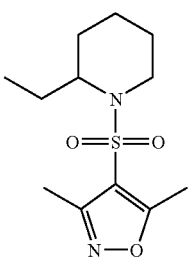 | H |
| 54 | —OCH₂—CH₃ | —(CH₂)₃—CH₃ | 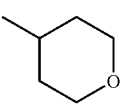 | H |

TABLE I-continued

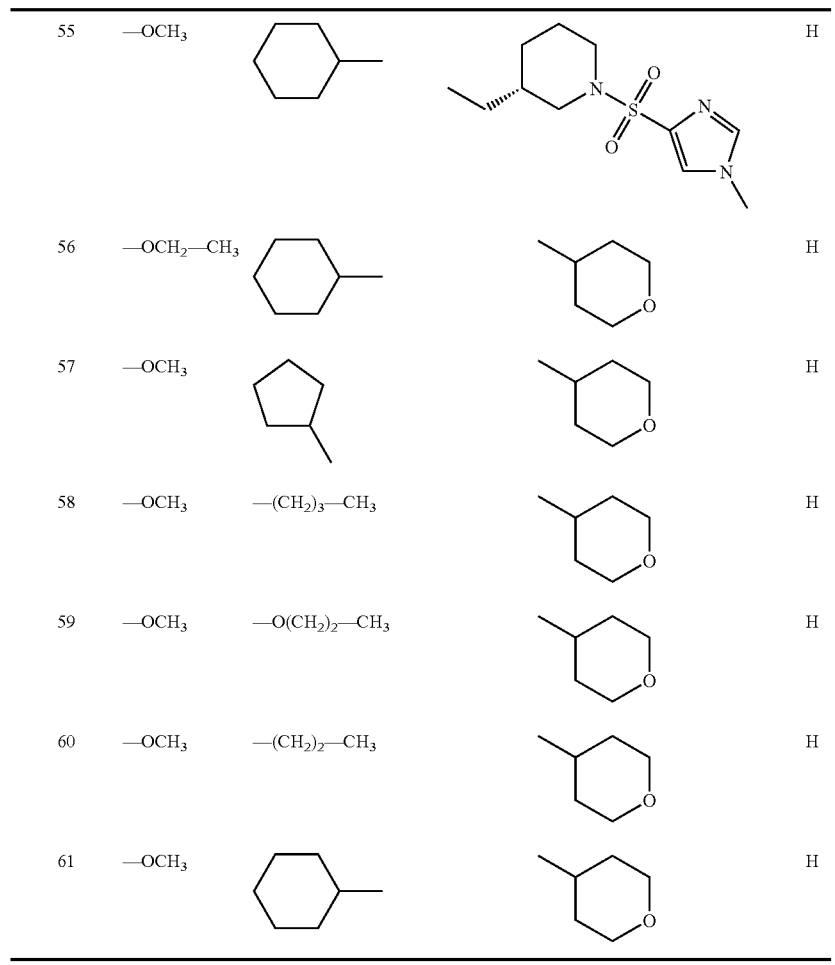

| Compound N° | p | Salt | Synthesis pathway | Analytical data | Nomenclature |
|---|---|---|---|---|---|
| 1 | 2 | — | Example 1 | MP = 88° C. $\alpha_D$ = +4° (c = 1, MeOH) MH+ = 538.8 at t = 6.52 min | 4-((S)-1-cyclopropylpiperidin-3-ylmethyl)piperazine-1-carboxylic acid [4-(5-cyclohexyl-2-methoxyphenyl)thiazol-2-yl]amide |
| 2 | 2 | — | Example 2 | MP = 134° C. MH+ = 568.7 at t = 7.61 min | 4-(1-isopropylcarbamoylpiperidin-3-yl)piperazine-1-carboxylic acid [4-(5-cyclohexyl-2-methoxyphenyl)thiazol-2-yl]amide |
| 3 | 2 | — | Example 3 | MP = 138° C. MH+ = 588.8 at t = 7.49 min | 4-(1-cyclopropanesulphonylpiperidin-4-yl)piperazine-1-carboxylic acid [4-(5-cyclohexyl-2-methoxyphenyl)thiazol-2-yl]amide |
| 4 | 2 | — | Example 4 | MH+ = 598.8 at t = 6.84 min | ethyl ester of 3-((R)-3-{4-[4-(5-cyclohexyl-2-methoxyphenyl)thiazol-2-ylcarbamoyl]piperazin-1-ylmethyl}piperidin-1-yl)propionic acid |
| 5 | 2 | — | Example 5 | MP = 144° C. MH+ = 570.7 at t = 6.64 min | 3-((R)-3-{4-[4-(5-cyclohexyl-2-methoxyphenyl)thiazol-2-ylcarbamoyl]piperazin-1-ylmethyl}piperidin-1-yl)propionic acid |
| 6 | 2 | — | Example 4 | MH+ = 612.8 at t = 6.62 min | ethyl ester of 4-((R)-3-{4-[4-(5-cyclohexyl-2-methoxyphenyl)thiazol-2-ylcarbamoyl]piperazin-1-ylmethyl}piperidin-1-yl)butyric acid |
| 7 | 2 | — | Example 5 | MP = 136° C. MH+ = 584.8 at t = 6.74 min | 4-((R)-3-{4-[4-(5-cyclohexyl-2-methoxyphenyl)thiazol-2-ylcarbamoyl]piperazin-1-ylmethyl}piperidin-1-yl)butyric acid |

TABLE I-continued

| | | | | | |
|---|---|---|---|---|---|
| 8 | 2 | — | Example 4 | MH+ = 626.8 at t = 6.71 min | ethyl ester of 5-((R)-3-{4-[4-(5-cyclohexyl-2-methoxyphenyl)thiazol-2-ylcarbamoyl]piperazin-1-ylmethyl}piperidin-1-yl)pentanoic acid |
| 9 | 2 | — | Example 5 | MP = 153° C. MH+ = 598.8 at t = 6.41 min | 5-((R)-3-{4-[4-(5-cyclohexyl-2-methoxyphenyl)thiazol-2-ylcarbamoyl]piperazin-1-ylmethyl}piperidin-1-yl)pentanoic acid |
| 10 | 2 | — | Example 6 | MP = 110° C. MH+ = 483.7 at t = 7.65 min | 4-cyclohexylpiperazine-1-carboxylic acid [4-(5-cyclohexyl-2-methoxyphenyl)thiazol-2-yl]amide |
| 11 | 2 | — | Example 6 | MP = 226° C. MH+ = 485.7 at t = 7.42 min | 4-(tetrahydropyran-4-yl)piperazine-1-carboxylic acid [4-(5-cyclohexyl-2-methoxyphenyl)thiazol-2-yl]amide |
| 12 | 2 | HCl | Example 1 | MH+ = 568.8 at t = 7.61 min | 4-((S)-1-cyclopropylpiperidin-3-ylmethyl)piperazine-1-carboxylic acid [4-(5-cyclohexyl-2-methoxyphenylthiazol-2-yl]amide |
| 13 | 2 | — | Example 7 | MP = 276° C. MH+ = 513.7 at t = 9.88 min | 4-(tetrahydropyran-4-carbonyl)piperazine-1-carboxylic acid [4-(5-cyclohexyl-2-methoxyphenyl)thiazol-2-yl]amide |
| 14 | 2 | — | Example 9 | MP = 134° C. MH+ = 555.8 at t = 6.57 min | 4-((S)-1-carbamoylmethylpiperidin-3-ylmethyl)piperazine-1-carboxylic acid [4-(5-cyclohexyl-2-methoxyphenyl)thiazol-2-yl]amide |
| 15 | 2 | — | Example 5 | MP = 180° C. MH+ = 556.7 at t = 7.29 min | ((S)-3-{4-[4-(5-cyclohexyl-2-methoxyphenyl)thiazol-2-ylcarbamoyl]piperazin-1-ylmethyl}piperidin-1-yl)acetic acid |
| 16 | 2 | TFA | Example 1 | MP = 139° C. MH+ = 556.8 at t = 7.02 min | 4-((S)-1-cyclopropylpiperidin-3-ylmethyl)piperazine-1-carboxylic acid [4-(5-cyclohexyl-2-methoxyphenyl)-5-fluorothiazol-2-yl]amide |
| 17 | 2 | — | Example 8 | MP = 114° C. MH+ = 499.7 at t = 7.75 min | 4-(tetrahydropyran-4-ylmethyl)piperazine-1-carboxylic acid [4-(5-cyclohexyl-2-methoxyphenyl)thiazol-2-yl]amide |
| 18 | 2 | — | Example 4 | MP = 78° C. MH+ = 584.8 at t = 7.06 min | ethyl ester of ((S)-3-{4-[4-(5-cyclohexyl-2-methoxyphenyl)thiazol-2-ylcarbamoyl]piperazin-1-ylmethyl}piperidin-1-yl)acetic acid |
| 19 | 2 | — | Example 10 | MP = 88° C. MH+ = 551.8 at t = 5.66 min | 4-[(R)-1-(2-cyanoethyl)piperidin-3-ylmethyl]piperazine-1-carboxylic acid [4-(5-cyclohexyl-2-methoxyphenyl)thiazol-2-yl]amide |
| 20 | 2 | — | Example 5 | MH+ = 569.8 at t = 6.99 min | sodium salt of 3-((R)-3-{4-[4-(5-cyclohexyl-2-methoxyphenyl)thiazol-2-ylcarbamoyl]piperazin-1-ylmethyl}piperidin-1-yl)propionic acid |
| 21 | 2 | — | Example 9 | MH+ = 569.8 at t = 6.66 min | 4-[(R)-1-(2-carbamoylethyl)piperidin-3-ylmethyl]piperazine-1-carboxylic acid [4-(5-cyclohexyl-2-methoxyphenyl)thiazol-2-yl]amide |
| 22 | 2 | — | Example 1 | MH+ = 552.8 at t = 7.98 min | 4-((R)-1-cyclopropylpiperidine-3-carbonyl)piperazine-1-carboxylic acid [4-(5-cyclohexyl-2-methoxyphenyl)thiazol-2-yl]amide |
| 23 | 2 | — | Example 1 | MP = 86° C. MH+ = 526.8 at t = 6.92 min | 4-((S)-1-cyclopropylpiperidin-3-ylmethyl)piperazine-1-carboxylic acid [4-(5-butyl-2-ethoxyphenyl)thiazol-2-yl]amide |
| 24 | 2 | — | Example 1 | MP = 71° C. MH+ = 538.8 at t = 6.92 min | 4-((S)-1-cyclopropylpiperidin-3-ylmethyl)piperazine-1-carboxylic acid [4-(5-cyclopentyl-2-ethoxyphenyl)thiazol-2-yl]amide |
| 25 | 2 | — | Example 1 | MP = 89° C. MH+ = 512.7 at t = 6.6 min | 4-((S)-1-cyclopropylpiperidin-3-ylmethyl)piperazine-1-carboxylic acid [4-(5-butyl-2-methoxyphenyl)thiazol-2-yl]amide |
| 26 | 2 | — | Example 6 | MP = 106° C. MH+ = 537.7 at t = 7.67 min | 4-((S)-1-cyanomethylpiperidin-3-ylmethyl)piperazine-1-carboxylic acid [4-(5-cyclohexyl-2-methoxyphenyl)thiazol-2-yl]amide |
| 27 | 2 | — | Example 1 | MP = 141° C. MH+ = 524.7 at t = 7.41 min | 4-((R)-1-cyclopropylpiperidin-3-yl)piperazine-1-carboxylic acid [4-(5-cyclohexyl-2-methoxyphenyl)thiazol-2-yl]amide |

TABLE I-continued

| | | | | | |
|---|---|---|---|---|---|
| 28 | 2 | — | Example 1 | MP = 106° C.<br>MH+ = 524.7<br>at t = 6.59 min | 4-(1-cyclopropylpiperidin-4-yl)piperazine-1-carboxylic acid [4-(5-cyclohexyl-2-methoxyphenyl)thiazol-2-yl]amide |
| 29 | 2 | — | Example 3 | MP = 114° C.<br>MH+ = 602.8<br>at t = 7.8 min | 4-((S)-1-cyclopropanesulphonylpiperidin-3-ylmethyl)piperazine-1-carboxylic acid [4-(5-cyclohexyl-2-methoxyphenyl)thiazol-2-yl]amide |
| 30 | 2 | — | Example 11 | MH+ = 574.8<br>at t = 8.12 min | 4-((S)-1-phenylpiperidin-3-ylmethyl)piperazine-1-carboxylic acid [4-(5-cyclohexyl-2-methoxyphenyl)thiazol-2-yl]amide |
| 31 | 2 | — | Example 3 | MP = 210° C. | 2-{4-[4-(5-cyclohexyl-2-methoxyphenyl)thiazol-2-ylcarbamoyl]piperazin-1-ylmethyl}piperidine-1-sulphonic acid |
| 32 | 2 | — | Example 8 | MH+ = 542.8<br>at t = 6.42 min | 4-[(S)-1-(2-hydroxyethyl)piperidin-3-ylmethyl]piperazine-1-carboxylic acid [4-(5-cyclohexyl-2-methoxyphenyl)thiazol-2-yl]amide |
| 33 | 2 | — | Example 6 | MP = 204° C.<br>MH+ = 533.7<br>at t = 7.65 min | 4-(1,1-dioxohexahydro-1$\lambda^6$-thiopyran-4-yl)piperazine-1-carboxylic acid [4-(5-cyclohexyl-2-methoxyphenyl)thiazol-2-yl]amide |
| 34 | 2 | — | Example 3 | MH+ = 594.7<br>at t = 8.25 min | 4-[(S)-1-(2,2,-trifluoroacetyl)piperidin-3-ylmethyl]piperazine-1-carboxylic acid [4-(5-cyclohexyl-2-methoxyphenyl)thiazol-2-yl]amide |
| 35 | 2 | — | Example 6 | MH+ = 503.7<br>at t = 7.61 min | 4-(tetrahydropyran-4-yl)piperazine-1-carboxylic acid [4-(5-cyclohexyl-2-methoxyphenyl)-5-fluorothiazol-2-yl]amide |
| 36 | 2 | — | Example 6 | MP = 207° C.<br>MH+ = 499.7<br>at t = 7.29 min | 4-(4-hydroxycyclohexyl)piperazine-1-carboxylic acid [4-(5-cyclohexyl-2-methoxyphenyl)-5-thiazol-2-yl]amide |
| 37 | 2 | — | Example 2 | MP = 145° C.<br>MH+ = 605.8<br>at t = 11.78 min | 4-((S)-1-dimethylsulphamoylpiperidin-3-ylmethyl)piperazine-1-carboxylic acid [4-(5-cyclohexyl-2-methoxyphenyl)thiazol-2-yl]amide |
| 38 | 2 | — | Example 6 | MP = 166° C.<br>MH+ = 554.8<br>at t = 9.24 min | 4-(1,2,2,6,6-pentamethylpiperidin-4-yl)piperazine-1-carboxylic acid [4-(5-cyclohexyl-2-methoxyphenyl)thiazol-2-yl]amide |
| 39 | 2 | — | Example 6 | MP = 189° C.<br>MH+ = 540.8<br>at t = 6.16 min | 4-(2,2,6,6-tetramethylpiperidin-4-yl)piperazine-1-carboxylic acid [4-(5-cyclohexyl-2-methoxyphenyl)thiazol-2-yl]amide |
| 40 | 2 | — | Example 8 | MP = 98° C.<br>MH+ = 527.7<br>at t = 7.98 min | 4-(2,2-dimethyltetrahydropyran-4-ylmethyl)piperazine-1-carboxylic acid [4-(5-cyclohexyl-2-methoxyphenyl)thiazol-2-yl]amide |
| 41 | 2 | — | Example 6 | MP = 118° C.<br>MH+ = 501.7<br>at t = 7.97 min | 4-(tetrahydrothiopyran-4-yl)piperazine-1-carboxylic acid [4-(5-cyclohexyl-2-methoxyphenyl)thiazol-2-yl]amide |
| 42 | 2 | — | Example 10 | MH+ = 580.7<br>at t = 7.32 min | 4-[(S)-1-(2H-tetrazol-5-ylmethyl)piperidin-3-ylmethyl]piperazine-1-carboxylic acid [4-(5-cyclohexyl-2-methoxyphenyl)thiazol-2-yl]amide |
| 43 | 2 | TFA | Example 3 | MH+ = 690.3<br>at t = 1.78 min<br>(method B) | 4-[1-(5-chloro-1,3-dimethyl-1H-pyrazole-4-sulphonyl)piperidin-2-ylmethyl]piperazine-1-carboxylic acid [4-(5-cyclohexyl-2-methoxyphenyl)thiazol-2-yl]amide |
| 44 | 2 | TFA | Example 3 | MH+ = 656.3<br>at t = 1.70 min<br>(method B) | 4-[1-(1,3-dimethyl-1H-pyrazole-4-sulphonyl)piperidin-2-ylmethyl]piperazine-1-carboxylic acid [4-(5-cyclohexyl-2-methoxyphenyl)thiazol-2-yl]amide |
| 45 | 2 | TFA | Example 3 | MH+ = 656.3<br>at t = 1.71 min<br>(method B) | 4-[1-(1,5-dimethyl-1H-pyrazole-4-sulphonyl)piperidin-2-ylmethyl]piperazine-1-carboxylic acid [4-(5-cyclohexyl-2-methoxyphenyl)thiazol-2-yl]amide |
| 46 | 2 | TFA | Example 3 | MH+ = 642.3<br>at t = 1.68 min<br>(method B) | 4-[1-(1-methyl-1H-pyrazole-4-sulphonyl)piperidin-2-ylmethyl]piperazine-1-carboxylic acid [4-(5-cyclohexyl-2-methoxyphenyl)thiazol-2-yl]amide |
| 47 | 2 | TFA | Example 3 | MH+ = 643.3<br>at t = 1.95 min<br>(method B) | 4-[1-(5-methylisoxazole-4-sulphonyl)piperidin-2-ylmethyl]piperazine-1-carboxylic acid [4-(5-cyclohexyl-2-methoxyphenyl)thiazol-2-yl]amide |

TABLE I-continued

| | | | | | |
|---|---|---|---|---|---|
| 48 | 2 | TFA | Example 3 | MH+ = 642.3 at t = 1.69 min (method B) | 4-[1-(1-methyl-1H-pyrazole-4-sulphonyl)piperidin-2-ylmethyl]piperazine-1-carboxylic acid [4-(5-cyclohexyl-2-methoxyphenyl)thiazol-2-yl]amide |
| 49 | 2 | TFA | Example 3 | MH+ = 605.3 at t = 1.73 min (method B) | 4-(1-dimethylsulphamoylpiperidin-2-ylmethyl)piperazine-1-carboxylic acid [4-(5-cyclohexyl-2-methoxyphenyl)thiazol-2-yl]amide |
| 50 | 2 | TFA | Example 3 | MH+ = 644.3 at t = 1.80 min (method B) | 4-[1-(2,2,2-trifluoroethanesulphonyl)piperidin-2-ylmethyl]piperazine-1-carboxylic acid [4-(5-cyclohexyl-2-methoxyphenyl)thiazol-2-yl]amide |
| 51 | 2 | — | Example 3 | MH+ = 668.3 at t = 1.83 min (method B) | 4-[1-(4-methoxy-benzenesulphonyl)piperidin-2-ylmethyl]piperazine-1-carboxylic acid [4-(5-cyclohexyl-2-methoxyphenyl)thiazol-2-yl]amide |
| 52 | 2 | — | Example 6 | MP = 190° C. MH+ = 485.7 at t = 10.3 min | 4-(tetrahydropyran-4-yl)piperazine-1-carboxylic acid [4-(5-cyclopentyl-2-ethoxyphenyl)thiazol-2-yl]amide |
| 53 | 2 | TFA | Example 3 | MH+ = 657.3 at t = 1.81 min (method B) | 4-[1-(3,5-dimethylisoxazole-4-sulphonyl)piperidin-2-ylmethyl]piperazine-1-carboxylic acid [4-(5-cyclohexyl-2-methoxyphenyl)thiazol-2-yl]amide |
| 54 | 2 | — | Example 6 | MP = 171° C. MH+ = 473.7 at t = 10.92 min | 4-(tetrahydropyran-4-yl)piperazine-1-carboxylic acid 4-(5-butyl-2-ethoxyphenyl)thiazol-2-yl]amide |
| 55 | 2 | — | Example 3 | MH+ = 642.8 at t = 7.61 min | 4-[(S)-1-(1-methyl-1H-imidazole-4-sulphonyl)piperidin-3-ylmethyl]piperazine-1-carboxylic acid [4-(5-cyclohexyl-2-methoxyphenyl)thiazol-2-yl]amide |
| 56 | 2 | — | Example 6 | MH+ = 499.7 at t = 7.63 min | 4-(tetrahydropyran-4-yl)piperazine-1-carboxylic acid [4-(5-cyclopentyl-2-ethoxyphenyl)thiazol-2-yl]amide |
| 57 | 2 | — | Example 6 | MH+ = 471.6 at t = 7.03 min | 4-(tetrahydropyran-4-yl)piperazine-1-carboxylic acid [4-(5-cyclopentyl-2-methoxyphenyl)thiazol-2-yl]amide |
| 58 | 2 | — | Example 6 | MH+ = 459.6 at t = 7.02 min | 4-(tetrahydropyran-4-yl)piperazine-1-carboxylic acid [4-(5-butyl-2-methoxyphenyl)thiazol-2-yl]amide |
| 59 | 2 | — | Example 6 | MH+ = 461.6 at t = 6.41 min | 4-(tetrahydropyran-4-yl)piperazine-1-carboxylic acid [4-(2-methoxy-5-propoxyphenyl)thiazol-2-yl]amide |
| 60 | 2 | — | Example 6 | MH+ = 445.6 at t = 6.64 min | 4-(tetrahydropyran-4-yl)piperazine-1-carboxylic acid [4-(5-propyl-2-methoxyphenyl)thiazol-2-yl]amide |
| 61 | 3 | — | Example 6 | MH+ = 499.7 at t = 7.39 min | 4-(tetrahydropyran-4-yl)[1,4]diazepane-1-carboxylic acid [4-(5-cyclohexyl-2-methoxyphenyl)thiazol-2-yl]amide |

The compounds according to the invention were used in pharmacological tests to determine the modulator effect thereof on the activity of chemokine receptors.

Chemokines are low molecular weight proteins which belong to the category of pro-inflammatory cytokines and are involved in the chemotactism of leukocytes and endothelial cells. Chemokines control a number of biological processes and are associated with inflammatory disorders appearing during stress conditions, with wounds or with infections; modulation of the effects of chemokines allows pathologies such as asthma, arthritis, allergies, auto-immune diseases, atherosclerosis or angiogenesis to be prevented or treated (C. D. Paavola et al., J. Biol. Chem., 1998, 273, (50), 33157-33165).

Chemokines include hMCP-1 (human monocyte chemotactic protein) which belongs to the CC chemokine group and is a natural agonist of the CCR2b receptor.

The inhibiting activity of the compounds according to the invention was measured on cells expressing the human CCR2b receptor. The concentration of natural hMCP-1 agonist which inhibited 50% ($Cl_{50}$) of the activity of the CCR2b receptor was 0.57 nM. The compounds according to the invention had a $Cl_{50}$ which was generally in the range 0.1 μM to 0.1 nM, preferably in the range 100 nM to 0.1 nM.

The following are brought into contact for 1 h 30 minutes at ambient temperature, in Millipore GF/B filter plates (ref. MAFBNOB 10 or 50): 50 μl of compound at $3 \times 10^{-5}$ M in the reaction buffer or cold MCP-1 range ((R & D Systems). Recombinant human MCP-1) (final concentration of compound: $10^{-5}$ M), and 50 μl of iodinated MCP-1 ($[^{125}I]$-MCP-1 human recombinant Bolton+Hunter labelled (Amersham)) at 0.3 nM in distilled water (final concentration of iodinated MCP-1: 0.1 nM), and 50 μl of CHO-K1-CCR2B cells (obtained from Euroscreen Brussels, Belgium) at $6 \times 10^5$ cells/ml (final concentration in the reaction buffer: $3 \times 10^5$ cells/wells). The filters were saturated beforehand with 100 μl of PEI at a final concentration of 0.0125% in PBS, for 72 h at 4° C., and the PEI was removed by filtration. The content of the wells was filtered and washed twice with the reaction buffer, and the filters were left to dry overnight. The following day, 20 μl/well of "Wallac Optiphase Super Mix" scintillant were dispensed. The filters were impregnated for 1 to 2 h and then counted with Trilux Iodine 125 for 1 min.

Reaction buffer=PBS buffer, 50 nM Hepes, 1 mM $CaCl_2$, 5 mM $MgCl_2$, 0.5% fatty acid-free BSA, adjusted to pH 7.4.

As an example, compound No 9 had a $Cl_{50}$ of 4 nM, compound No 10 had a $Cl_{50}$ of 53 nM, compound No 22 had a $Cl_{50}$ of 4 nM, compound No 40 had a $Cl_{50}$ of 82 nM, compound No 41 had a $Cl_{50}$ of 39 nM, compound No 33 had a $Cl_{50}$ of 20 nM, compound No 11 had a $Cl_{50}$ of 20 nM, compound No 23 had a $Cl_{50}$ of 8 nM, compound No 29 had a $Cl_{50}$ of 50 nM and compound No 45 had a $Cl_{50}$ of 73 nM.

The compounds according to the invention can thus be used to prepare drugs, in particular drugs which are antagonists to the effect of chemokines.

In another aspect, then, the present invention pertains to drugs which comprise a compound of formula (I) or an addition salt thereof with a pharmaceutically acceptable acid, or a hydrate or a solvate.

Said drugs can be used in therapy, in particular in the prevention and treatment of various pathologies such as:

acute and chronic immuno-inflammatory diseases and syndromes such as atherosclerosis, restenosis, chronic pulmonary disease, in particular COPD (chronic obstructive pulmonary disease); respiratory distress syndrome; bronchial hyperactivity; colitis; silicosis; fibrous pathologies, pulmonary fibrosis, cystic fibrosis; viral or bacterial infections, AIDS, meningitis, malaria, leprosy, tuberculosis, herpes, cytomegalovirus infections; septic shock, septicaemia, endotoxic shock; graft rejection; bone pathologies such as osteoporosis, osteoarthritis; conjunctivitis; atypical or contact dermatitis; eczema; glomerulonephritis; pancreatitis; ulcerous colitis, autoimmune diseases such as rheumatoid polyarthritis, multiple sclerosis, amyotrophic lateral sclerosis, Crohn's disease, lupus erythematosus, scleredema, psoriasis; Parkinson's disease; Alzheimer's disease; diabetes; cachexia; obesity;

the treatment of pain, in particular neuropathic and inflammatory pain;

allergic diseases such as allergic respiratory diseases, asthma, rhinitis, pulmonary hypersensitivity, retarded hypersensitivity;

diseases and disorders involving angiogenic processes, such as cancers (intratumoral angiogenesis), retinal disorders (age-related macular degeneracy: ARMD);

cardiac diseases: haemodynamic shock; cardiac ischemia; post-ischemic re-infusion seizures; myocardial infarctus; coronary thrombosis, cardiac insufficiency, angina pectoris.

In a further aspect, the present invention concerns pharmaceutical compositions comprising a compound according to the invention as the active principle. Said pharmaceutical compositions contain an effective dose of at least one compound according to the invention, or a pharmaceutically acceptable salt, a hydrate or a solvate of said compound, and at least one pharmaceutically acceptable excipient.

Selection of said excipients depends on the desired form of administration and pharmaceutical form, from the usual excipients which are known to the skilled person.

In the pharmaceutical compositions of the present invention for oral, sublingual, subcutaneous, intramuscular, intravenous, topical, local, intratracheal, intranasal, transdermal or rectal administration, the active principle of formula (I) above, or any salt, solvate or hydrate thereof, may be administered in a unitary administration form, mixed with conventional pharmaceutical excipients, to animals and humans for prophylaxis or to treat the problems or diseases mentioned above.

Suitable unitary administration forms include oral forms such as tablets, soft or hard gelules, powders, granules and oral solutions or suspensions, sublingual, buccal, intratracheal, intraocular, intranasal or inhaled forms of administration, topical, transdermal, subcutaneous, intramuscular or intravenous forms of administration, rectal forms of administration and implants. For topical application, the compounds according to the invention may be used in creams, gels, pomades or lotions.

As an example, a unitary form of administration of a compound of the invention in the form of a tablet may comprise the following components:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropyl-methylcellulose | 2.25 mg |
| Magnesium stearate | 3.0 mg. |

Orally, the dose of active principle administered per day may be from 0.1 to 1000 mg/kg, in one or more doses.

Particular cases may arise in which higher or lower doses are appropriate: such doses do not fall within the scope of the invention. Usually, the appropriate dose for each patient is determined by the physician as a function of the mode of administration and the patient's weight and response.

In a still further aspect, the present invention also concerns a method for treating the disorders indicated above, which comprises administering an effective dose of a compound according the invention, or one of its pharmaceutically acceptable salts or hydrates or solvates, to a patient.

What is claimed is:

1. A compound of formula (I):

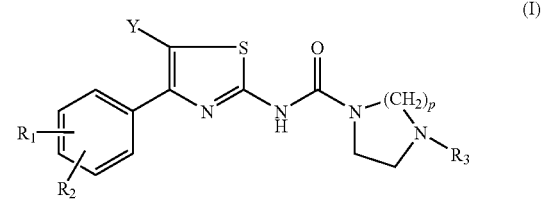

(I)

wherein:

$R_1$ represents a hydrogen atom, a halogen atom, a $(C_1-C_8)$ alkyl, trifluoro$(C_1-C_4)$alkyl, —OH, —O—$(C_1-C_8)$ alkyl, —O—trifluoro$(C_1-C_8)$alkyl, —O—$(C_1-C_8)$ alkyl-$(C_3-C_{10})$cycloalkyl, —O—$(C_3-C_{10})$cycloalkyl, —O—$CH_2$—CH=$CH_2$ or —S—$(C_1-C_4)$alkyl group;

$R_2$ represents a hydrogen atom, a halogen atom, an —OH, $(C_1-C_8)$alkyl, trifluoro$(C_1-C_4)$alkyl, perfluoro$(C_1-C_4)$ alkyl, $(C_3-C_{10})$cycloalkyl, —O—$(C_1-C_8)$alkyl, —O— $(C_1-C_8)$alkyl$(C_3-C_{10})$cycloalkyl, —O—$(C_3-C_{10})$cycloalkyl, —O—$CH_2$—CH=$CH_2$ or —$(C_1-C_8)$alkyl $(C_3-C_8)$cycloalkyl group;

Y represents a hydrogen atom or a halogen atom;

p represents 2 or 3;

$R_3$ represents:

a1) a group of formula —$(CH_2)_a$-A in which a represents 1, 2, 3 or 4, and A is selected from the group consisting of:

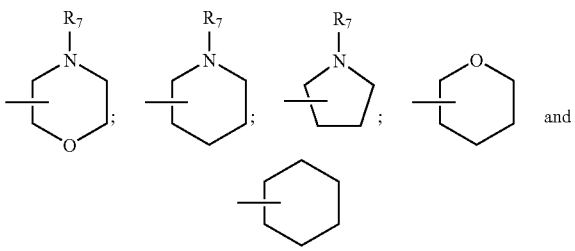

in which R$_7$ is selected from the group consisting of:
—(C$_1$-C$_8$)alkyl-COO—(C$_1$-C$_8$)alkyl,
—(C$_3$-C$_6$)cycloalkyl,
-COO—(C$_3$-C$_6$)cycloalkyl,
—CO—NH((C$_1$-C$_5$)alkyl),
—(C$_1$-C$_8$)alkyl-CN,
—(C$_1$-C$_8$)alkylimidazole,
—(C$_1$-C$_8$)alkyl-COOH,
—(C$_1$-C$_8$)alkyl-CO—NH$_2$,
—(C$_1$-C$_8$)alkyl-CO—NH((C$_1$-C$_5$)alkyl,
—(C$_1$-C$_8$)alkyl-CO—NH((C$_3$-C$_6$)cycloalkyl),
—(C$_1$-C$_8$)alkyl-CO—N((C$_1$-C$_5$)alkyl)((C$_3$-C$_6$)cycloalkyl),
—(C$_1$-C$_8$)alkyl-CO—N((C$_1$-C$_5$)alkyl)$_2$, and
—(C$_1$-C$_8$)alkyl-CO—N((C$_3$-C$_6$)cycloalkyl)$_2$;
and when two alkyl or cycloalkyl substituents are bonded to the nitrogen atom, they may be independently identical or different;
a2) a group of formula -CO(CH$_2$)$_b$-A in which b represents 0, 1, 2, 3 or 4, and A is selected from the group consisting of:

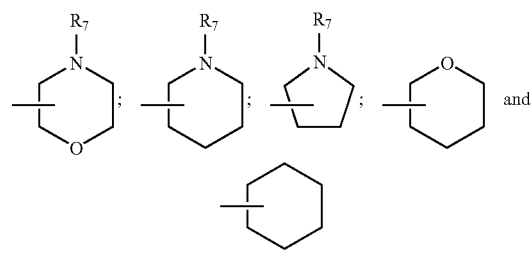

in which R$_7$ is as defined above;
a3) a group —B in which B is selected from the group consisting of:

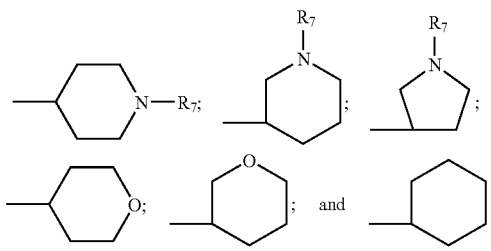

in which R$_7$ is as defined above;
or an acid addition salt thereof.

2. A compound according to claim 1, of formula (I.a):

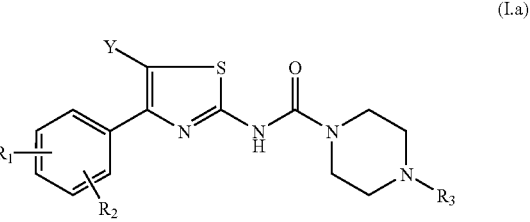

(I.a)

in which R$_1$, R$_2$, R$_3$ and Y are as defined in claim 1;
or an acid addition salt thereof.

3. A compound according to claim 2, of formula (I.a) wherein R$_1$ is in the 2-position and R$_2$ is in the 5-position;
or an acid addition salt thereof 4. A compound according to claim 1, wherein R$_1$ represents —O—(C$_1$-C$_8$)alkyl;
or an acid addition salt thereof.

5. A compound according to claim 1, wherein R$_2$ represents a (C$_1$-C$_8$)alkyl, (C$_3$-C$_{10}$)cycloalkyl, perfluoro(C$_1$-C$_4$)alkyl or —O—(C$_1$-C$_8$)alkyl group;
or an acid addition salt thereof.

6. A compound according to claim 5, wherein R$_2$ represents a (C$_1$-C$_8$)alkyl, (C$_3$-C$_{10}$)cycloalkyl or —O—(C$_1$-C$_8$)alkyl group;
or an acid addition salt thereof.

7. A compound according to claim 1, wherein R$_3$ represents a group of formula —(CH$_2$)$_a$-A in which a represents 1, 2, 3 or 4, and A is selected from the group consisting of:

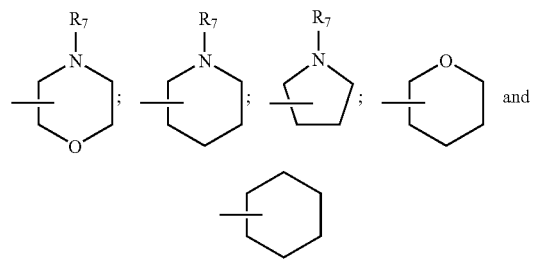

in which R$_7$ is as defined in claim 1;
or an acid addition salt thereof.

8. A compound according to claim 7, wherein A is selected from the group consisting of:

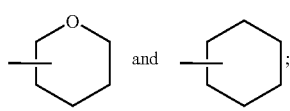

or an acid addition salt thereof.

9. A compound according to claim 1, wherein R$_3$ represents a group of formula —CO(CH$_2$)$_b$-A in which b represents 0, 1, 2, 3 or 4, and A is selected from the group consisting of:

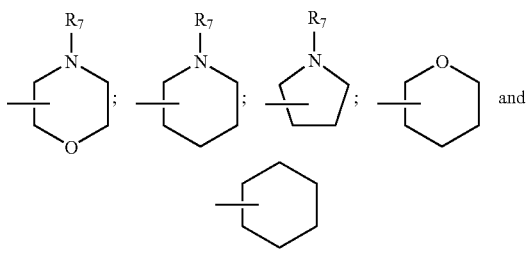

in which R_7 is as defined in claim 1;
or an acid addition salt thereof.

10. A compound according to claim 9, wherein A is selected from the group consisting of:

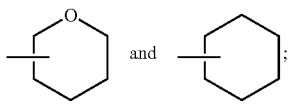

or an acid addition salt thereof.

11. A compound according to claim 1, wherein R_3 represents a group —B in which B is selected from the group consisting of:

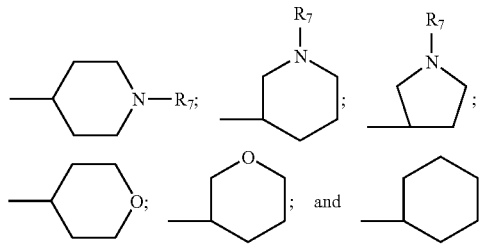

in which R_7 is as defined in claim 1;
or an acid addition salt thereof.

12. A compound according to claim 1, wherein R_7 is selected from the group consisting of:
—(C_1-C_8)alkyl-COO—(C_1-C_5)alkyl,
—(C_3-C_6)cycloalkyl,
—CO—NH((C_1-C_5)alkyl),
—(C_1-C_8)alkyl-CN,
—(C_1-C_8)alkyl-COOH, and
—(C_1-C_8)alkyl-CO—NH_2,
and when two alkyl or cycloalkyl substituents are bonded to a nitrogen atom, they may be independently identical or different;
or an acid addition salt thereof.

13. A compound according to claim 1, selected from the group consisting of:
4-((S)-1-cyclopropylpiperidin-3-ylmethyl)piperazine-1-carboxylic acid [4-(5-cyclohexyl-2-methoxyphenyl)thiazol-2-yl]amide;
4-(1-isopropylcarbamoylpiperidin-3-yl)piperazine-1-carboxylic acid [4-(5-cyclohexyl-2-methoxyphenyl)thiazol-2-yl]amide;
the ethyl ester of 3-((R)-3-{4-[4-(5-cyclohexyl-2-methoxyphenyl)thiazol-2-ylcarbamoyl]piperazin-1-ylmethyl}piperidin-1-yl)propionic acid;
3-((R)-3-{4-[4-(5-cyclohexyl-2-methoxyphenyl)thiazol-2-ylcarbamoyl]piperazin-1-ylmethyl}piperidin-1-yl)propionic acid;
the ethyl ester of 4-((R)-3-{4-[4-(5-cyclohexyl-2-methoxyphenyl)thiazol-2-ylcarbamoyl]piperazin-1-ylmethyl}piperidin-1-yl)butyric acid;
4-((R)-3-{4-[4-(5-cyclohexyl-2-methoxyphenyl)thiazol-2-ylcarbamoyl]piperazin-1-ylmethyl}piperidin-1-yl)butyric acid;
the ethyl ester of 5-((R)-3-{4-[4-(5-cyclohexyl-2-methoxyphenyl)thiazol-2-ylcarbamoyl]piperazin-1-ylmethyl}piperidin-1-yl)pentanoic acid;
5-((R)-3-{4-[4-(5-cyclohexyl-2-methoxyphenyl)thiazol-2-ylcarbamoyl]piperazin-1-ylmethyl}piperidin-1-yl)pentanoic acid;
4-cyclohexylpiperazine-1-carboxylic acid [4-(5-cyclohexyl-2-methoxyphenyl)thiazol-2-yl]amide; and
4-(tetrahydropyran-4-yl)piperazine-1-carboxylic acid [4-(5-cyclohexyl-2-methoxyphenyl)thiazol-2-yl]amide;
or an acid addition salt, hydrate or solvate thereof.

14. A compound which is:
4-(tetrahydropyran-4-yl)piperazine-1-carboxylic acid [4-(5-cyclohexl-2-methoxyphenyl)thiazol-2-yl]amide;
or a pharmaceutically acceptable salt thereof.

15. A compound according to claim 1, selected from the group consisting of:
4-((S)-1-cyclopropylpiperidin-3-ylmethyl)piperazine-1-carboxylic acid [4-(5-cyclohexl-2-methoxyphenyl)thiazol-2-yl]amide;
4-(tetrahydropyran-4-carbonyl)piperazine-1-carboxylic acid [4-(5-cyclohexl-2-methoxyphenyl)thiazol-2-yl]amide;
4-((S)-1-carbamoylmethylpiperidin-3-ylmethyl)piperazine-1-carboxylic acid [4-(5-cyclohexl-2-methoxyphenyl)thiazol-2-yl]amide;
((S)-3-{4-[4-(5-cyclohexl-2-methoxyphenyl)thiazol-2-ylcarbamoyl]piperazin-1-ylmethyl}piperidin-1-yl)acetic acid;
4-((S)-1-cyclopropylpiperidin-3-ylmethyl)piperazine-1-carboxylic acid [4-(5-cyclohexl-2-methoxyphenl)-5-fluorothiazol-2-yl]amide;
4-(tetrahydropyran-4-ylmethyl)piperazine-1-carboxylic acid [4-(5-cyclohexl-2-methoxyphenyl)thiazol-2-yl]amide;
the ethyl ester of ((S)-3-{4-[4-(5-cyclohexl-2-methoxyphenyl)thiazol-2-ylcarbamoyl]piperazin-1-ylmethyl}piperidin-1-yl)acetic acid;
4-[(R)-1-(2-cyanoethyl)piperidin-3-ylmethyl]piperazine-1-carboxylic acid [4-(5-cyclohexl-2-methoxyphenyl)thiazol-2-yl]amide;
4-[(R)-1-(2-carbamoylethyl)piperidin-3-ylmethyl]piperazine-1-carboxylic acid [4-(5-cyclohexl-2-methoxyphenyl)thiazol-2-yl]amide;
4-((R)-1-cyclopropylpiperidine-3-carbonyl)piperazine-1-carboxylic acid [4-(5-cyclohexl-2-methoxyphenyl)thiazol-2-yl]amide;
4-((S)-1-cyclopropylpiperidin-3-ylmethyl)piperazine-1-carboxylic acid [4-(5-butyl-2-ethoxyphenyl)thiazol-2-yl]amide;
4-((S)-1-cyclopropylpiperidin-3-ylmethyl)piperazine-1-carboxylic acid [4-(5-cyclopentl-2-ethoxyphenyl)thiazol-2-yl]amide;
4-((S)-1-cyclopropylpiperidin-3-ylmethyl)piperazine-1-carboxylic acid [4-(5-butyl-2-methoxyphenyl)thiazol-2-yl]amide;

4-((S)-1-cyanomethylpiperidin-3-ylmethyl)piperazine-1-carboxylic acid [4-(5-cyclohexl-2-methoxyphenyl)thiazol-2-yl]amide;

4-((R)-1-cyclopropylpiperidin-3-yl)piperazine-1-carboxylic acid [4-(5-cyclohexl-2-methoxyphenyl)thiazol-2-yl]amide;

4-(1-cyclopropylpiperidin-4-yl)piperazine-1-carboxylic acid [4-(5-cyclohexl-2-methoxyphenyl)thiazol-2-yl]amide;

4-(tetrahydropyran-4-yl)piperazine-1-carboxylic acid [4-(5-cyclohexl-2-methoxyphenl)-5-fluorothiazol-2-yl]amide;

4-[1-(1-methyl-1H-imidazole-4-sulphonyl)piperidin-2-ylmethyl]piperazine-1-carboxylic acid [4-(5-cyclohexl-2-methoxyphenyl)thiazol-2-yl]amide;

4-(tetrahydropyran-4-yl)piperazine-1-carboxylic acid [4-(5-cyclopentl-2-ethoxyphenyl)thiazol-2-yl]amide;

4-(tetrahydropyran-4-yl)piperazine-1-carboxylic acid [4-(5-butyl-2-ethoxyphenyl)thiazol-2-yl]amide;

4-(tetrahydropyran-4-yl)piperazine-1-carboxylic acid [4-(5-cyclohexl-2-3ethoxyphenyl)thiazol-2-yl]amide;

4-(tetrahydropyran-4-yl)piperazine-1-carboxylic acid [4-(5-cyclopentl-2-methoxyphenyl)thiazol-2-yl]amide;

4-(tetrahydropyran-4-yl)piperazine-1-carboxylic acid [4-(5-butyl-2-methoxyphenyl)thiazol-2-yl]amide;

4-(tetrahydropyran-4-yl)piperazine-1-carboxylic acid [4-(2-methoxy-5-propoxyphenyl)thiazol-2-yl]amide;

4-(tetrahydropyran-4-yl)piperazine-1-carboxylic acid [4-(5-propyl-2-methoxyphenyl)thiazol -2-yl]amide; and 4-(tetrahydropyran-4-yl)[1,4]diazepane-1-carboxylic acid [4-(5-cyclohexl-2-methoxyphenyl)thiazol-2-yl]amide;

or an acid addition salt thereof.

16. A compound selected from the group consisting of:

4-(1,1-dioxohexahydro-1$\lambda^6$-thiopyran-4-yl)piperazine-1-carboxylic acid [4-(5-cyclohexl-2-methoxyphenyl)thiazol-2-yl]amide;

4-(4-hydroxycyclohexyl)piperazine-1-carboxylic acid [4-(5-cyclohexl-2-methoxyphenyl)thiazol-2-yl]amide;

4-(1,2,2,6,6-pentamethylpiperidin-4-yl)piperazine-1-carboxylic acid [4-(5-cyclohexl-2-methoxyphenyl)thiazol-2-yl]amide;

4-(2,2,6,6-tetramethylpiperidin-4-yl)piperazine-1-carboxylic acid [4-(5-cyclohexl-2-methoxyphenyl)thiazol-2-yl]amide;

4-(2,2-dimethyltetrahydropyran-4-ylmethyl)piperazine-1-carboxylic acid [445-cyclohexl-2-methoxyphenyl)thiazol-2-yl]amide; and 4-(tetrahydrothiopyran-4-yl)piperazine-1-carboxylic acid [4-(5-cyclohexl-2-methoxyphenyl)thiazol-2-yl]amide.

17. A pharmaceutical composition comprising a compound of formula (I) according to claim 1, or a pharmaceutically acceptable salt of said compound, as well as at least one pharmaceutically acceptable excipient.

\* \* \* \* \*

UNITED STATES PATENT AND TRADEMARK OFFICE
CERTIFICATE OF CORRECTION

| | | |
|---|---|---|
| PATENT NO. | : 7,825,112 B2 | |
| APPLICATION NO. | : 12/146898 | |
| DATED | : November 2, 2010 | |
| INVENTOR(S) | : Pierre Casellas et al. | |

It is certified that error appears in the above-identified patent and that said Letters Patent is hereby corrected as shown below:

In column 11, line 24, delete "$R_{11}, R_{12}$" and insert -- $R'_1, R'_2$ --, therefor.

In column 13, line 23-24, delete "diisopropylthylamine" and insert -- diisopropylethylamine --, therefor.

In column 16, line 48, delete "diisopropylthylamine" and insert -- diisopropylethylamine --, therefor.

In column 17, line 7, delete "Column;" and insert -- Column: --, therefor.

In column 39-40, line 17, delete "methoxyphenylthiazol-" and insert -- methoxyphenyl)thiazol- --, therefor.

In column 41-42, line 25, delete "(2,2,-" and insert -- (2,2,2- --, therefor.

In column 41-42, line 35, delete "-5-thiazol" and insert -- thiazol --, therefor.

In column 43-44, line 35, delete "cyclopentyl-2-" and insert -- cyclohexyl-2- --, therefor.

In column 44, line 60, delete "$10^5$" and insert -- $10^6$ --, therefor.

In column 47, line 25, in claim 1, delete "alkyl," and insert -- alkyl), --, therefor.

In column 48, line 20, in claim 3, after "thereof" insert -- . --, therefor.

In column 50, line 20, in claim 13, delete "salt, hydrate or solvate" and insert -- salt --, therefor.

In column 50, line 24, in claim 14, delete "cyclohexl" and insert -- cyclohexyl --, therefor.

In column 50, line 29, in claim 15, delete "cyclohexl" and insert -- cyclohexyl --, therefor.

In column 50, line 32, in claim 15, delete "cyclohexl" and insert -- cyclohexyl --, therefor.

Signed and Sealed this
Twenty-fourth Day of May, 2011

David J. Kappos
*Director of the United States Patent and Trademark Office*

CERTIFICATE OF CORRECTION (continued)
U.S. Pat. No. 7,825,112 B2

In column 50, line 35, in claim 15, delete "cyclohexl" and insert -- cyclohexyl --, therefor.

In column 50, line 37, in claim 15, delete "cyclohexl" and insert -- cyclohexyl --, therefor.

In column 50, line 41, in claim 15, delete "cyclohexl" and insert -- cyclohexyl --, therefor.

In column 50, line 41, in claim 15, delete "methoxyphenl" and insert -- methoxyphenyl --, therefor.

In column 50, line 44, in claim 15, delete "cyclohexl" and insert -- cyclohexyl --, therefor.

In column 50, line 46, in claim 15, delete "cyclohexl" and insert -- cyclohexyl --, therefor.

In column 50, line 50, in claim 15, delete "cyclohexl" and insert -- cyclohexyl --, therefor.

In column 50, line 54, in claim 15, delete "cyclohexl" and insert -- cyclohexyl --, therefor.

In column 50, line 57, in claim 15, delete "cyclohexl" and insert -- cyclohexyl --, therefor.

In column 50, line 63, in claim 15, delete "cyclopentl" and insert -- cyclopentyl --, therefor.

In column 51, line 2, in claim 15, delete "cyclohexl" and insert -- cyclohexyl --, therefor.

In column 51, line 5, in claim 15, delete "cyclohexl" and insert -- cyclohexyl --, therefor.

In column 51, line 8, in claim 15, delete "cyclohexl" and insert -- cyclohexyl --, therefor.

In column 51, line 11, in claim 15, delete "cyclohexl" and insert -- cyclohexyl --, therefor.

In column 51, line 11, in claim 15, delete "methoxyphenl" and insert -- methoxyphenyl --, therefor.

In column 51, line 14, in claim 15, delete "cyclohexl" and insert -- cyclohexyl --, therefor.

In column 51, line 17, in claim 15, delete "cyclopentl" and insert -- cyclopentyl --, therefor.

In column 51, line 21, in claim 15, delete "cyclohexl" and insert -- cyclohexyl --, therefor.

In column 51, line 21, in claim 15, delete "3ethoxyphenyl" and insert -- 3-ethoxyphenyl --, therefor.

In column 51, line 23, in claim 15, delete "cyclopentl" and insert -- cyclopentyl --, therefor.

In column 52, line 4, in claim 15, delete "cyclohexl" and insert -- cyclohexyl --, therefor.

In column 52, line 8, in claim 16, delete "cyclohexl" and insert -- cyclohexyl --, therefor.

In column 52, line 11, in claim 16, delete "cyclohexl" and insert -- cyclohexyl --, therefor.

In column 52, line 13, in claim 16, delete "cyclohexl" and insert -- cyclohexyl --, therefor.

In column 52, line 16, in claim 16, delete "cyclohexl" and insert -- cyclohexyl --, therefor.

In column 52, line 19, in claim 16, delete "[445-cyclohexl" and insert -- [4-(5-cyclohexyl --, therefor.

CERTIFICATE OF CORRECTION (continued)
U.S. Pat. No. 7,825,112 B2

In column 52, line 22, in claim 16, delete "cyclohexl" and insert -- cyclohexyl --, therefor.